United States Patent
Herman et al.

(10) Patent No.: US 10,949,581 B2
(45) Date of Patent: Mar. 16, 2021

(54) TOOL FOR CONFIGURING COMPUTATIONAL MODELS

(71) Applicant: SAP SE, Walldorf (DE)

(72) Inventors: Dave Herman, Easton, PA (US); Mert Karakilic, Coquitlam (CA)

(73) Assignee: SAP SE, Walldorf (DE)

( * ) Notice: Subject to any disclaimer, the term of this patent is extended or adjusted under 35 U.S.C. 154(b) by 679 days.

(21) Appl. No.: 15/705,153

(22) Filed: Sep. 14, 2017

(65) Prior Publication Data

US 2019/0080031 A1 Mar. 14, 2019

(51) Int. Cl.
| | |
|---|---|
| *G06Q 40/00* | (2012.01) |
| *G06F 30/20* | (2020.01) |
| *G06F 17/18* | (2006.01) |
| *G06Q 40/08* | (2012.01) |
| *G06Q 10/06* | (2012.01) |
| *G06F 111/02* | (2020.01) |
| *G06F 111/10* | (2020.01) |
| *G06Q 10/04* | (2012.01) |
| *G06Q 40/02* | (2012.01) |
| *G16H 50/30* | (2018.01) |
| *G16H 50/20* | (2018.01) |

(52) U.S. Cl.
CPC .............. *G06F 30/20* (2020.01); *G06F 17/18* (2013.01); *G06Q 10/0635* (2013.01); *G06Q 40/00* (2013.01); *G06Q 40/08* (2013.01); *G06F 2111/02* (2020.01); *G06F 2111/10* (2020.01); *G06Q 10/04* (2013.01); *G06Q 40/02* (2013.01); *G16H 50/20* (2018.01); *G16H 50/30* (2018.01)

(58) Field of Classification Search
None
See application file for complete search history.

(56) References Cited

U.S. PATENT DOCUMENTS

| | | | |
|---|---|---|---|
| 9,747,570 B1 | 8/2017 | Vescio | |
| 9,910,962 B1* | 3/2018 | Fakhrai-Rad | G16H 50/30 |
| 2005/0119922 A1* | 6/2005 | Eder | G06Q 10/06 705/7.31 |
| 2006/0100958 A1* | 5/2006 | Cheng | G06Q 10/0631 705/38 |
| 2007/0124236 A1* | 5/2007 | Grichnik | G06Q 40/025 705/38 |
| 2007/0208600 A1* | 9/2007 | Babus | G06Q 10/04 705/7.28 |

(Continued)

*Primary Examiner* — Kibrom K Gebresilassie
(74) *Attorney, Agent, or Firm* — Fountainhead Law Group P.C.

(57) ABSTRACT

Some embodiments provide a non-transitory machine-readable medium that stores a program. The program provides a client device a tool for configuring computational models. The program further receives, from the client device and through the tool, a selection of a set of external data sources. The program also receives, from the client device and through the tool, a plurality of weight values for a plurality of categories. The program further receives, from the client device and through the tool, a plurality of threshold values for the plurality of categories. The program also generates a plurality of computational models based on the set of external data sources, the plurality of weight values for the plurality of categories, and the plurality of threshold values for the plurality of categories.

20 Claims, 14 Drawing Sheets

(56) References Cited

U.S. PATENT DOCUMENTS

| | | | |
|---|---|---|---|
| 2010/0036684 A1* | 2/2010 | McNamee | G06Q 40/08 |
| | | | 705/4 |
| 2013/0085917 A1* | 4/2013 | Agarwal | G06Q 40/06 |
| | | | 705/35 |
| 2013/0297376 A1* | 11/2013 | Miller | G06Q 10/08 |
| | | | 705/7.28 |
| 2014/0143134 A1 | 5/2014 | Yan et al. | |
| 2015/0026027 A1 | 1/2015 | Priess et al. | |
| 2015/0148616 A1 | 5/2015 | Van Dongen et al. | |
| 2015/0310545 A1* | 10/2015 | deOliveira | G06Q 40/02 |
| | | | 705/35 |
| 2015/0324715 A1 | 11/2015 | Nelson et al. | |
| 2015/0339769 A1* | 11/2015 | deOliveira | G06Q 40/025 |
| | | | 705/38 |
| 2016/0239865 A1* | 8/2016 | Song | G06Q 30/0251 |
| 2017/0006135 A1 | 1/2017 | Siebel et al. | |
| 2017/0093905 A1 | 3/2017 | Ng et al. | |
| 2017/0161614 A1 | 6/2017 | Mehta et al. | |
| 2017/0242920 A1 | 8/2017 | Neland | |
| 2017/0255745 A1* | 9/2017 | Mihalef | G06F 17/11 |
| 2017/0255867 A1 | 9/2017 | Ramachandran et al. | |
| 2017/0277857 A1* | 9/2017 | De La Torre | G06F 19/324 |
| 2018/0357714 A1* | 12/2018 | So | G06Q 40/025 |
| 2019/0079990 A1 | 3/2019 | Herman et al. | |
| 2019/0188797 A1* | 6/2019 | Przechocki | G06N 20/00 |

* cited by examiner

TOOL FOR CONFIGURING COMPUTATIONAL MODELS

SUMMARY

In some embodiments, a non-transitory machine-readable medium stores a program. The program provides a client device a tool for configuring computational models. The program further receives, from the client device and through the tool, a selection of a set of external data sources. The program also receives, from the client device and through the tool, a plurality of weight values for a plurality of categories. The program further receives, from the client device and through the tool, a plurality of threshold values for the plurality of categories. The program also generates a plurality of computational models based on the set of external data sources, the plurality of weight values for the plurality of categories, and the plurality of threshold values for the plurality of categories.

In some embodiments, the program may further receive, from the client device and through the tool, a set of field definitions. Generating the plurality of computational models may be further based on the set of field definitions. A field definition in the set of field definitions may specify a name, a category in the plurality of categories, and a field type. The field definition may specify the field type as a text field type. The field definition may further specify a set of mappings between a set of text values and a set of values. The field definition may specify the field type as a numeric field type. The field definition may further specify a weight, a low threshold value, and a high threshold value.

In some embodiments, the plurality of threshold values for the plurality of categories may be a first plurality of threshold values. The program may further receive, from the client device and through the tool, a second plurality of threshold values for the plurality of categories. Generating the plurality of computational models may be further based on the second plurality of threshold values for the plurality of categories. The program may further receive, from the client device and through the tool, a first threshold value for an overall score and a second threshold value for the overall score. Generating the plurality of computational models may be further based on the first threshold value for the overall score and the second threshold value for the overall score.

In some embodiments, a method provides a client device a tool for configuring computational models. The method further receives, from the client device and through the tool, a selection of a set of external data sources. The method also receives, from the client device and through the tool, a plurality of weight values for a plurality of categories. The method further receives, from the client device and through the tool, a plurality of threshold values for the plurality of categories. The method also generates a plurality of computational models based on the set of external data sources, the plurality of weight values for the plurality of categories, and the plurality of threshold values for the plurality of categories.

In some embodiments, the method may further receive, from the client device and through the tool, a set of field definitions. Generating the plurality of computational models may be further based on the set of field definitions. A field definition in the set of field definitions may specify a name, a category in the plurality of categories, and a field type. The field definition may specify the field type as a text field type. The field definition may further specify a set of mappings between a set of text values and a set of values. The field definition may specify the field type as a numeric field type. The field definition may further specify a weight, a low threshold value, and a high threshold value.

In some embodiments, the plurality of threshold values for the plurality of categories may be a first plurality of threshold values. The method may further receive, from the client device and through the tool, a second plurality of threshold values for the plurality of categories. Generating the plurality of computational models may be further based on the second plurality of threshold values for the plurality of categories. The method may further receive, from the client device and through the tool, a first threshold value for an overall score and a second threshold value for the overall score. Generating the plurality of computational models may be further based on the first threshold value for the overall score and the second threshold value for the overall score.

In some embodiments, a system includes a set of processing units and a non-transitory machine-readable medium that stores instructions. The instructions cause at least one processing unit to provide a client device a tool for configuring computational models. The instructions further cause the at least one processing unit to receive, from the client device and through the tool, a selection of a set of external data sources. The instructions also cause the at least one processing unit to receive, from the client device and through the tool, a plurality of weight values for a plurality of categories. The instructions further cause the at least one processing unit to receive, from the client device and through the tool, a plurality of threshold values for the plurality of categories. The instructions also cause the at least one processing unit to generate a plurality of computational models based on the set of external data sources, the plurality of weight values for the plurality of categories, and the plurality of threshold values for the plurality of categories.

In some embodiments, the instructions may further cause the at least one processing unit to receive, from the client device and through the tool, a set of field definitions. Generating the plurality of computational models may be further based on the set of field definitions. A field definition in the set of field definitions may specify a name, a category in the plurality of categories, and a field type. The field definition may specify the field type as a text field type. The field definition may further specify a set of mappings between a set of text values and a set of values. The field definition may specify the field type as a numeric field type. The field definition may further specify a weight, a low threshold value, and a high threshold value.

In some embodiments, the plurality of threshold values for the plurality of categories may be a first plurality of threshold values. The instructions may further cause the at least one processing units to receive, from the client device and through the tool, a second plurality of threshold values for the plurality of categories. Generating the plurality of computational models may be further based on the second plurality of threshold values for the plurality of categories.

The following detailed description and accompanying drawings provide a better understanding of the nature and advantages of the present invention.

DETAILED DESCRIPTION

In the following description, for purposes of explanation, numerous examples and specific details are set forth in order to provide a thorough understanding of the present invention. It will be evident, however, to one skilled in the art that the present invention as defined by the claims may include some or all of the features in these examples alone or in combination with other features described below, and may further include modifications and equivalents of the features and concepts described herein.

Described herein are techniques for configuring computational models for assessing risk (also referred to as risk models). In some embodiments, a computing system includes an application that provides a tool for a client device to use to configure computational models for assessing risk. Through the tool, a user of the client device may specify various configuration settings for such computational models. For instance, the user may specify types of external data (e.g., news articles, disaster alerts, compliance checks and/or reports, risk data associated with geographical regions, etc.) to be used by computational models, weight values for several risk categories (e.g., financial risk, operational risk, environmental risk, social risk, legal risk, regulatory risk, etc.), threshold values (e.g., a low threshold, a high threshold value) for each of the several risk categories, field definitions, etc. Based on the specified configuration settings, the computing system may generate several computational models that the computing system can use to calculate risk scores for entities. In some embodiments, a risk score for an entity represents a quantified potential for loss that may occur during procurement activities with the entity in a specified period of time.

In some embodiments, the computing system calculates a risk score for an entity based on computational models by using each computational model to calculate a risk score. Then, the computing system determines an overall risk score for the entity based on the calculated risk scores. An example computational model may calculate a risk score for an entity based on data associated with the entity. Another example computational model may calculate a risk score for an entity based on certain types of external data received from external data sources.

Figure 1:
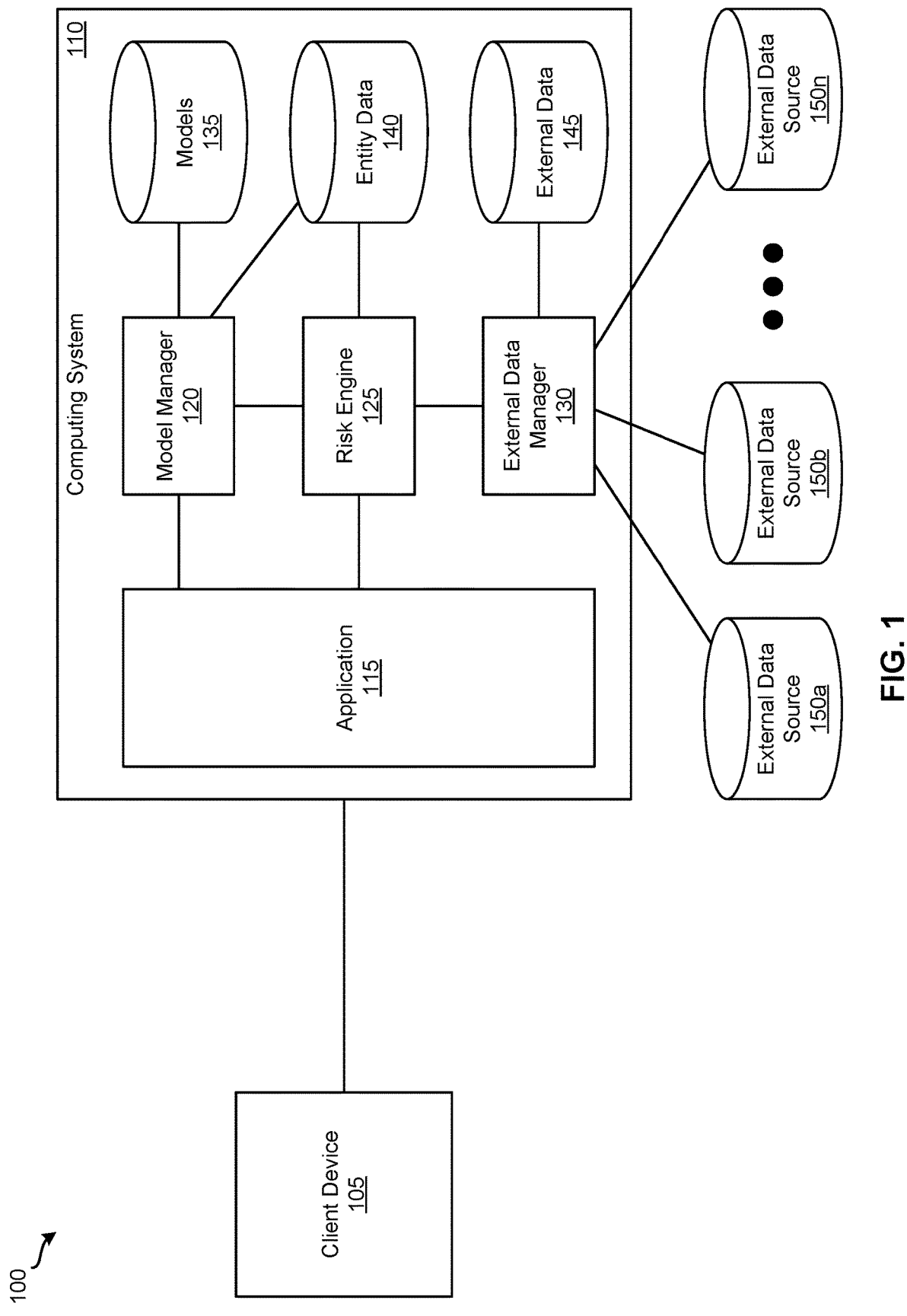
FIG. 1 illustrates a system for configuring computational models and calculating risk scores according to some embodiments.

FIG. 1 illustrates system 100 for configuring computational models and calculating risk scores according to some embodiments. As shown, system 100 includes client device 105, computing system 110, and external data sources 150a-n. Client device 105 is configured to communicate with and interact with computing system 110 (e.g., via a web browser operating on client device 105). For instance, client device 105 may access application 115 and a tool for configuring computational models provided by application 115.

A user of client device 105 may use the tool to specify configuration settings for computational models. Once the user has configured the computational models, the user of client device 105 may request application 115 to provide risk scores for entities based on the configured computational models.

External data sources 150a-n are configured to manage, store, and/or provide external data for computing system 110. In some embodiments, an external data source 150 may be a third-party database and/or service. Examples of types of external data stored and/or provided by external data sources 150a-n include global disaster data (e.g., disaster alerts), country risk data (e.g., risk data associated with geographical regions), incident data (e.g., news articles), corporation information data (e.g., compliance checks and/or reports), etc. Each external data source 150 may store and/or provide one or more types of external data.

In some embodiments, each item of incident data stored and/or provided by an external data source 150 may be associated with an incident type. Examples of incident types may include accident incidents, acquisition incidents, air traffic security risk incidents, anti-competitive behavior incidents, arrested incidents, arson incidents, asset freeze incidents, asset sales incidents, avalanche incidents, aviation disasters incidents, bad performance incidents, bankrupt incidents, bankruptcy incidents, blackout incidents, border issue incidents, business expansion incidents, buying selling stake incidents, buying stake incidents, buyout incidents, central bank reprimand incidents, charged incidents, chemical oil spill incidents, child abuse incidents, child labor incidents, child porn incidents, civil disobedience incidents, closed incidents, complaint incidents, conflict commodities incidents, conflict of interest incidents, convicted incidents, copyright violation incidents, corporate ban incidents, corporate crime incidents, corporate lawsuits incidents, corporate partnerships incidents, corporate waste management incidents, corruption incidents, court case incidents, credit downgrade incidents, credit rating downgrade entity incidents, crime incidents, criminal bribery incidents, criminal counterfeit incidents, criminal drug crime incidents, criminal environmental crime incidents, criminal fraud incidents, criminal homicide incidents, criminal issue incidents, criminal reference incidents, cyber breach incidents, dangerous gene mutation incidents, decertification incidents, decrease earning incidents, deteriorating financial situation incidents, disqualification incidents, distraint incidents, divestment incidents, Dodd-Frank Act incidents, downsizing incidents, drought and heat wave incidents, earthquake, eruption, and tsunami incidents, environmental disaster incidents, ethical practice incidents, explosion incidents, explosion accident incidents, external trade-regulator incidents, financial mechanism failure incidents, financial penalty incidents, financial regulator incidents, financial reporting fraud incidents, financing crime incidents, fine incidents, fire incidents, fire disasters incidents, flood incidents, food poisoning incidents, for sale incidents, fraud incidents, fraud forgery incidents, funding incidents, general strike incidents, geomagnetic storm incidents, government site hit incidents, government department incidents, hacker incidents, human organs trafficking incidents, human rights incidents, human trafficking incidents, hurricane incidents, identity theft incidents, illegal trade incidents, increase earnings incidents, industrial disasters incidents, industry regulator incidents, insider trading incidents, insolvency incidents, intellectual property infringement incidents, international sanction incidents, investigation incidents, joint venture incidents, kidnapping incidents, labor dispute incidents, labor issue incidents, labor violation incidents, landslide incidents, layoff incidents, leak incidents, legal issue incidents, legal reference incidents, leveraged buyout incidents, lightning incidents, liquidation incidents, liquidity crisis incidents, lost client incidents, lost employee incidents, management buyout incidents, maritime disaster incidents, maritime security risk incidents, merger acquisition incidents, merger incidents, meteorite impact incidents, militant incidents, mining disaster incidents, miscellaneous damage incidents, money laundering incidents, moved incidents, nepotism incidents, new sales contract incidents, nuclear accident incidents, Office of Foreign Asset Control (OFAC) incidents, organized crime incidents, Occupational Safety and Health Administration (OSHA) incidents, ownership change incidents, pedophile incidents, patent infringement incidents, pay ability incidents, plant disruption incidents, plant shutdown incidents, police site hit incidents, political exposure incidents, privatization incidents, probe incidents, product issue incidents, product recall incidents, project delay incidents, project failure incidents, protest or demonstration incidents, quality issue incidents, radioactive contamination incidents, railway disaster incidents, regulatory incidents, regulatory compliance issue incidents, regulatory site incidents, reprimand incidents, riot incidents, safety incidents, sanctioned country incidents, sanction incidents, sanction violation incidents, sandstorm incidents, selling stake incidents, senior management change incidents, sentence incidents, sexual assault incidents, shady practice incidents, slave labor incidents, snowstorm incidents, spinoff incidents, stock exchange incidents, storm incidents, tax issue incidents, terrorism incidents, terrorism financing incidents, thunderstorm incidents, tornado incidents, torture incidents, trademark infringement incidents, transportation delay incidents, tsunami incidents, unethical practice incidents, unrest incidents, vandalism incidents, vehicle technical failure incidents, violation incidents, volcanic eruption incidents, wanted person incidents, water damage incidents, wild and forest fire incidents, windstorm incidents, workplace discrimination incidents, workplace safety neglect incidents, etc.

As illustrated in FIG. 1, computing system 110 includes application 115, model manager 120, risk engine 125, external data manager 130, and storages 135-145. Models storage 135 is configured to store computational models. Entity data storage 140 may store data associated with entities. Examples of data associated with an entity include an entity identifier (ID) that uniquely identifies the entity, a legal name, other names (e.g., a trade style, a fictitious business name, etc.) associated with the entity, an address, a city, a state or province, a country, contact information (e.g., a phone number, a fax number, etc.), a tax ID, etc. In some embodiments, entity data storage 140 may also store risk data associated with entities. Examples of risk data associated with an entity include a risk level, a risk score, a revenue impact, a revenue impact in terms of currency (e.g., United States dollars (USD), etc.), a spend amount, a current of the spend amount, a period of the spend amount and revenue impact, a relationship type, a relationship status, a risk rating, user-defined fields, etc. In some such embodiments, such risk data associated with an entity is provided by a user of client device 105. External data storage 145 can store external data from external data sources 150a-n. In some embodiments, storages 135-145 are implemented in a single physical storage while, in other embodiments, storages 135-145 may be implemented across several physical storages. While FIG. 1 shows storages 135-145 as part of computing system 110, one of ordinary skill in the art will appreciated that storages 135, 140, and/or 145 may be external to in computing system 110 in some embodiments.

Application 115 may be a software application operating on (e.g., hosted on) computing system 110 that may be accessed by client device 105. In some embodiments, application 115 provides client device 105 a set of application program interfaces (APIs) through which client device 105 interacts with application 115. Application 115 may be any number of different types of applications. For instance, application 115 may be an analytics application, a data management application, a human capital management application, an enterprise management application, a customer relationship management application, a financial management application, a sourcing event management application, a supplier management application, a supply chain configuration management application, a contracts management application, a financial supply chain management application, a transactional processor and storage hub for purchasing and financial documents, a payment processing application, a catalog hosting and management application, a supplier application for discovering new sales opportunities, a managed procurement desk application for shared services providers, a unified procurement application for guided buying. etc.

Application 115 may provide client device 105 a tool for configuring computational models. In some embodiments, application 115 provides the tool via a graphical user interface (GUI). When configuring computational models, application 115 may receive from client device 105 configuration settings for computational models. Then, application 115 may receive a request from client device 105 to generate computational models based on the configuration settings. In response to the request, application 115 sends the request along with the configuration settings to model manager 120. Application 115 can receive from client device 105 updated configuration settings for computational models. In such cases, application 115 sends the request and the updated configuration settings to model manager 120.

Application 115 can also process requests for risk information from client device 105. For example, application 115 may receive from client device 105 a request for risk information for an entity. Examples of risk information for an entity include an overall risk score associated with the entity, a risk level associated with the entity, risk scores for risk categories associated with the entity, risk levels for the risk categories associated with the entity, a history of risk scores (e.g., overall risk scores, risk scores for risk categories, etc.) associated with the entity, etc. In response to such a request, application 115 sends the request to risk engine 125 for processing. Once the request is processed, application 115 receives the risk information for the entity from risk engine 125. Application 115 then provides the risk information for the entity to client device 105 for client device 105. In some embodiments, application 115 provides the risk information for the entity via a GUI. As another example, application 115 can receive a request from client device 105 a request for risk information for entities associated with a user of client device 105. In response, application 115 sends the request to risk engine 125 for processing. After risk engine 125 processes the request, application 115 receives from risk engine 125 the risk information for the entities associated with the user of client device 105. Next, application 115 provides client device 105 the risk information for the entities associate with the user of client device 105. In some embodiments, application 115 provides the risk information via a GUI.

Model manager 120 is responsible for managing computational models. For instance, model manager 120 may receive from application 115 configuration settings for computational models that were specified by a user (e.g., a user of client device 105) as well as a request to generate computational models. In response to the request, model manager 120 generates a set of computational models associated with the user of client device 105 based on the configuration settings and then stores the set of computational models in models storage 135. Model manager 120 can generate the set of computational models by retrieving entity data (e.g., entity data for entities associated with the user) from entity data storage 140, enriching the entity data, and storing the enriched entity data along with the set of computational models in models storage 135. In some embodiments, the set of computational models that model manager 120 generates include different types of computational models for different risk categories. One type of computational model, referred to as an entity computational model, determines risk scores for an entity based on attributes associated with an entity. Another type of computational model, referred to as an incident computational model, determines risk scores for an entity based on incidents associated with the entity. Additional and/or different types of computational models may be used in different embodiments. Examples of risk categories include a financial risk category, an operational risk category, an environmental risk category, a social risk category, a legal risk category, a regulatory risk category, etc., or a combination thereof.

In some embodiments, an entity computational model for a particular risk category can be expressed according to the following equation (1):

$$R_c = \frac{\sum_{i=1}^{n} (\theta_i \times b_i)}{m}$$

where $R_c$ is the entity computational model risk score for the particular risk category, $b_i$ is a value associated with an entity attribute, $\theta_i$ is a weight associated with the entity attribute, and m is an amount of risk mitigated for the particular risk category. In some instances, a weight associated with an entity attribute may be derived (e.g., by model manager 120) from a history of the attribute's contribution to risk outcomes and an analysis of past distributions of values of the entity attribute for different entities. In other instances, a weight associated with an entity attribute can be defined. For example, a user of client device 105 may provide weight values for entity attributes during the configuration of computational models. An amount of risk mitigated for a particular risk category can be provided by a user of client device 105. For instance, a user of client device 105 may provide amount of risk mitigated for a particular risk category by using the computational model configuration tool during configuration of computational models or using the computational model configuration tool to update the configuration of computational models.

In some embodiments, an incident computational model for a particular risk category can be expressed according to the following equation (2):

$$R_i = \frac{\sum_{i=1}^{n} (boost_i \times probability_i \times impact_i)}{m}$$

where $R_c$ is the incident computational model risk score for the particular risk category, i is an incident, $boost_i$ is a weight associated with the incident based on the incident type of the incident, $probability_i$ is a probability of the incident occurring, $impact_i$ is an impact of the occurrence of the incident, and m a percentage of risk mitigated for the particular risk category. In some instances, different weight values are determined (e.g., by model manager 120) for different incident types. A weight value for a particular incident type can be determined based on an analysis of patterns of historical occurrences of incidents of the particular type. An amount of risk mitigated for a particular risk category can be provided by a user of client device 105. For example, a user of client device 105 may provide amount of risk mitigated for a particular risk category by using the computational model configuration tool during configuration of computational models or using the computational model configuration tool to update the configuration of computational models.

In some instances, model manager 120 receives from application 115 updated configuration settings associated with a user (e.g., a user of client device 105) and a request to update a particular set of computational models. In response, model manager 120 accesses models storage 135, identifies the set of computational models associated with the user, and then updates them with the updated configuration settings. As another example, model manager 120 may receive from risk engine 125 a request for a set of computational models associated with a particular user stored in models storage 135. In response, model manager 120 accesses models storage 135, retrieves the set of computational models associated with the particular user, and sends them to risk engine 125.

In some cases, model manager 120 may receive from risk engine 125 requests for computational models associated with a user (e.g., a user of client device 105) and enriched entity data of entities associated with the user. In response, model manager 120 accesses models storage 135, and retrieves a set of computational models associated with the user and enriched entity data for a set of requested entities associated with the user. Model manager 120 then sends the set of computational models and enriched entity data to risk engine 125.

Risk engine 125 is configured to process requests for risk information for entities. For example, risk engine 125 may receive from application 115 a request for risk information for an entity associated with a user (e.g., a user of client device 105). As explained above, examples of risk information for an entity include an overall risk score associated with the entity, a risk level associated with the entity, risk scores for risk categories associated with the entity, risk levels for the risk categories associated with the entity, a history of risk scores (e.g., overall risk scores, risk scores for risk categories, etc.) associated with the entity, etc. In response to the request, risk engine 125 sends model manager 120 a request for the set of computational models associated with the user and the enriched entity data of the entity. Risk engine 125 then sends external data manager 130 a request for external data associated with the entity. Once risk engine 125 receives the set of computational models, the enriched entity data, and the external data, risk engine 125 determines risk information for the entity based on the data associated with the entity, the set or computational models, and the external data associated with the entity. Risk engine 125 sends the determined risk information for the entity to application 115.

Risk engine 125 may also generate risk scores (e.g., overall risk scores for entities, risk category risk scores for entities, etc.) in response to the occurrence of a variety of different events. For example, when a record for a new entity is created and stored in entity data storage 140, risk engine 125 generates risk scores for the entity based on the data in the created record for the new entity. Risk engine 125 may generate risk scores for an entity if any data in the record for the entity stored in entity data storage 140 is updated and/or modified. As another example, risk engine 125 may generate risk scores for one or more entities with records stored in entity data storage 140 after a user of client device 105 finishes providing configuration settings for computational models. If the user of client device 105 modifies the configuration settings for computational models, risk engine 125 can generate risk scores for one or more entities with records stored in entity data storage 140. In some embodiments, risk engine 125 generates risk scores for an entity when external data manager 130 receives new incident data (e.g., news articles) from external data sources 150a-n that are associated with the entity. Risk engine 125 can generate risk scores for an entity when external data manager 130 receives risk data associated with a geographical region in which the entity is located or disaster data associated with a geographical region in which the entity is located.

External data manager 130 is configured to manage external data stored in external data storage 145. For example, external data manager 130 may receive and/or retrieve items of external data from external data sources 150a-n and store them in external data 145. As mentioned above, in some embodiments, each item of external data received from an external data source 150 may be associated with an incident type. In some such embodiments, when external data manager 130 receives an item of incident data (e.g., a news article) from an external data source 150, external data manager 130 determines an incident type of the item of incident data and determines a risk category associated with the item of incident data based on a mapping between incident types and risk categories and then stores that information along with the news article in external data storage 145.

In some embodiments, external data manager 130 handles requests from risk engine 125 for external data associated with an entity. When external data manager 130 requests such a request, external data manage 130 accesses external data storage 145 and retrieves a set of external data associated with the entity. Then, external data manager 130 sends the set of external data to risk engine 125.

For instance, a mapping between incident types and risk categories may specify that the following incident types mentioned above are mapped to an operational risk category: accident incidents, air traffic security risk incidents, avalanche incidents, aviation disasters incidents, bad performance incidents, blackout incidents, border issue incidents, civil disobedience incidents, closed incidents, distraint incidents, drought and heat wave incidents, earthquake, eruption, and tsunami incidents, explosion incidents, explosion accident incidents, financial mechanism failure incidents, fire incidents, fire disasters incidents, flood incidents, food poisoning incidents, general strike incidents, geomagnetic storm incidents, hurricane incidents, industrial disasters incidents, labor dispute incidents, labor issue incidents, labor violation incidents, landslide incidents, layoff incidents, leak incidents, lightning incidents, lost employee incidents, maritime disaster incidents, maritime security risk incidents, meteorite impact incidents, militant incidents, mining disaster incidents, miscellaneous damage incidents, moved incidents, nuclear accident incidents, plant disruption incidents, plant shutdown incidents, product issue incidents, product recall incidents, project delay incidents, project failure incidents, protest or demonstration incidents, quality issue incidents, railway disaster incidents, riot incidents, safety incidents, sandstorm incidents, senior management change incidents, snowstorm incidents, storm incidents, terrorism incidents, thunderstorm incidents, tornado incidents, transportation delay incidents, tsunami incidents, unrest incidents, vandalism incidents, vehicle technical failure incidents, volcanic eruption incidents, water damage incidents, wild and forest fire incidents, and windstorm incidents.

In addition, the mapping between incident types and risk categories may specify that the following incident types mentioned above are mapped a financial risk category: acquisition incidents, asset freeze incidents, asset sales incidents, bankrupt incidents, bankruptcy incidents, business expansion incidents, buying selling stake incidents, buying stake incidents, buyout incidents, central bank reprimand incidents, corporate partnerships incidents, credit downgrade incidents, credit rating downgrade entity incidents, decrease earning incidents, deteriorating financial situation incidents, divestment incidents, downsizing incidents, financial regulator incidents, for sale incidents, funding incidents, increase earnings incidents, insolvency incidents, joint venture incidents, leveraged buyout incidents, liquidity crisis incidents, lost client incidents, management buyout incidents, merger acquisition incidents, merger incidents, new sales contract incidents, ownership change incidents, privatization incidents, selling stake incidents, and spinoff incidents.

The mapping between incident types and risk categories may also specify that the following incident types mentioned above are mapped a legal and regulatory risk category: anti-competitive behavior incidents, arrested incidents, arson incidents, charged incidents, child labor incidents, complaint incidents, conflict of interest incidents, convicted incidents, copyright violation incidents, corporate ban incidents, corporate crime incidents, corporate lawsuits incidents, corruption incidents, court case incidents, crime incidents, criminal bribery incidents, criminal counterfeit incidents, criminal drug crime incidents, criminal environmental crime incidents, criminal fraud incidents, criminal homicide incidents, criminal issue incidents, criminal reference incidents, cyber breach incidents, decertification incidents, disqualification incidents, external trade-regulator incidents, financial penalty incidents, financial reporting fraud incidents, financing crime incidents, fine incidents, fraud incidents, fraud forgery incidents, government site hit incidents, government department incidents, hacker incidents, human organs trafficking incidents, human rights incidents, human trafficking incidents, identity theft incidents, illegal trade incidents, industry regulator incidents, insider trading incidents, intellectual property infringement incidents, international sanction incidents, investigation incidents, kidnapping incidents, legal issue incidents, legal reference incidents, liquidation incidents, money laundering incidents, nepotism incidents, OFAC incidents, organized crime incidents, OSHA incidents, pedophile incidents, patent infringement incidents, pay ability incidents, police site hit incidents, probe incidents, regulatory incidents, regulatory compliance issue incidents, regulatory site incidents, reprimand incidents, sanctioned country incidents, sanction incidents, sanction violation incidents, sentence incidents, sexual assault incidents, shady practice incidents, stock exchange incidents, tax issue incidents, terrorism financing incidents, torture incidents, trademark infringement incidents, unethical practice incidents, violation incidents, wanted person incidents, workplace discrimination incidents, and workplace safety neglect incidents.

Additionally, the mapping between incident types and risk categories may specify that the following incident types mentioned above are mapped an environmental and social risk category: chemical oil spill incidents, child abuse incidents, child porn incidents, conflict commodities incidents, corporate waste management incidents, dangerous gene mutation incidents, Dodd-Frank Act incidents, environmental disaster incidents, ethical practice incidents, political exposure incidents, radioactive contamination incidents, and slave labor incidents.

Figure 2A:
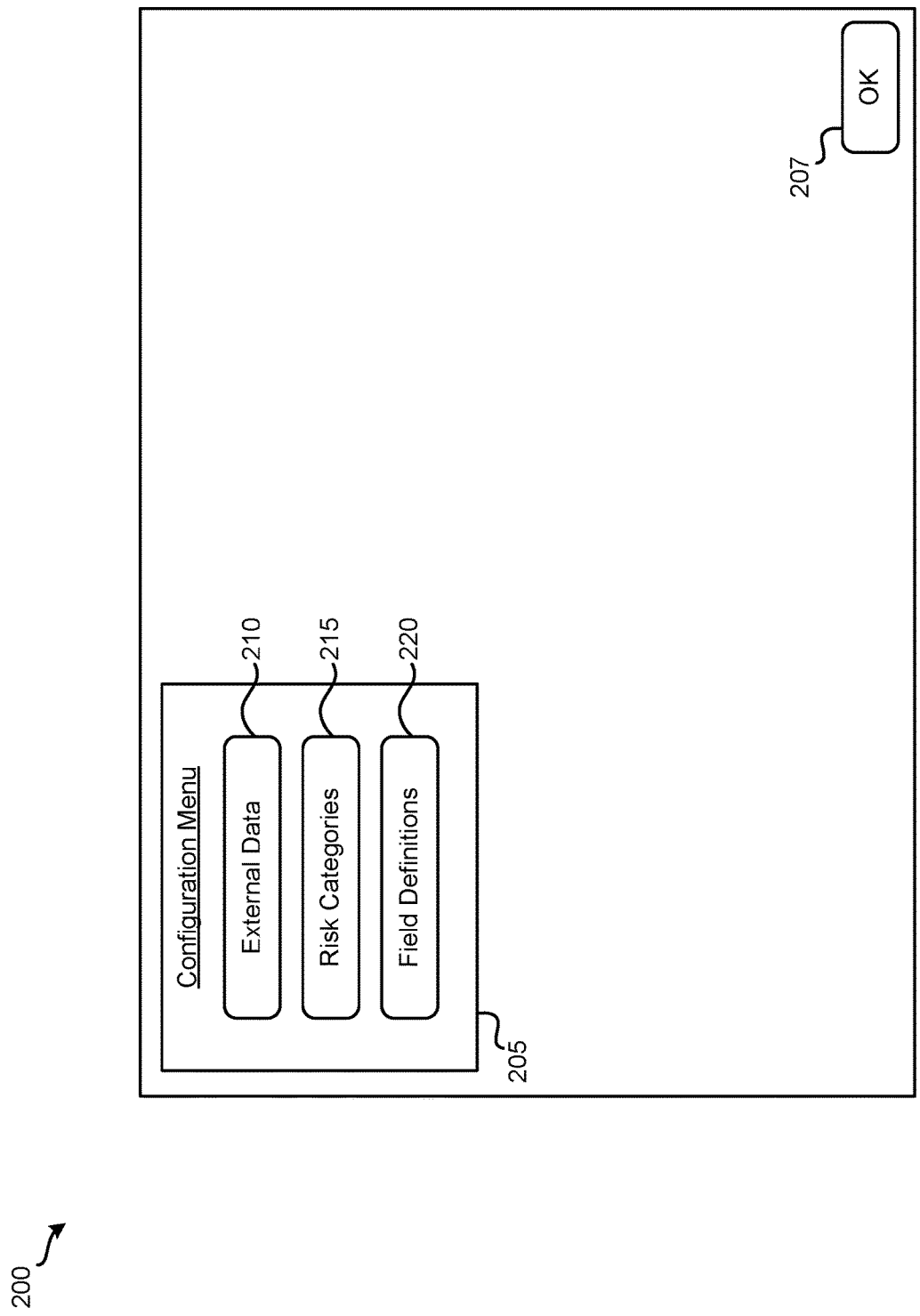
FIGS. 2A-2F illustrate a computational model configuration tool according to some embodiments.

An example computational model configuration operation will now be described by reference to FIGS. 1 and 2A-2F. FIGS. 2A-2F illustrate a computational model configuration tool provided through GUI 200 according to some embodiments. In this example, application 115 provides the tool to client device 105 via GUI 200. The example computational model configuration operation starts by a user of client device 105 accessing application 115 and requesting a computational model configuration tool. In response, application 115 provides client device with GUI 200, as illustrated in FIG. 2A, and client device 105 presents GUI 200 to the user (e.g., by displaying it on a display of client device 105). As shown, GUI 200 in FIG. 2A includes configuration menu 205 and selectable user interface (UI) item 207. Configuration menu 205 includes selectable UI items 210-220. UI item 210, when selected, causes GUI 200 to transition to a page for configuring external data for the computational models. UI item 215, when selected, causes application 115 to transition to a page of GUI 200 for configuring risk categories for the computational models. UI item 220, when selected, causes GUI 200 to transition to a page for configuring field definitions for the computational models. UI item 207, when selected, causes client device 105 to send application 115 a request to generate computational models based on the configuration settings specified through various configuration pages of GUI 200 described below. For this example, the user of client device 105 selects UI items 210 in order to configure external data for the computational models.

Figure 2B:
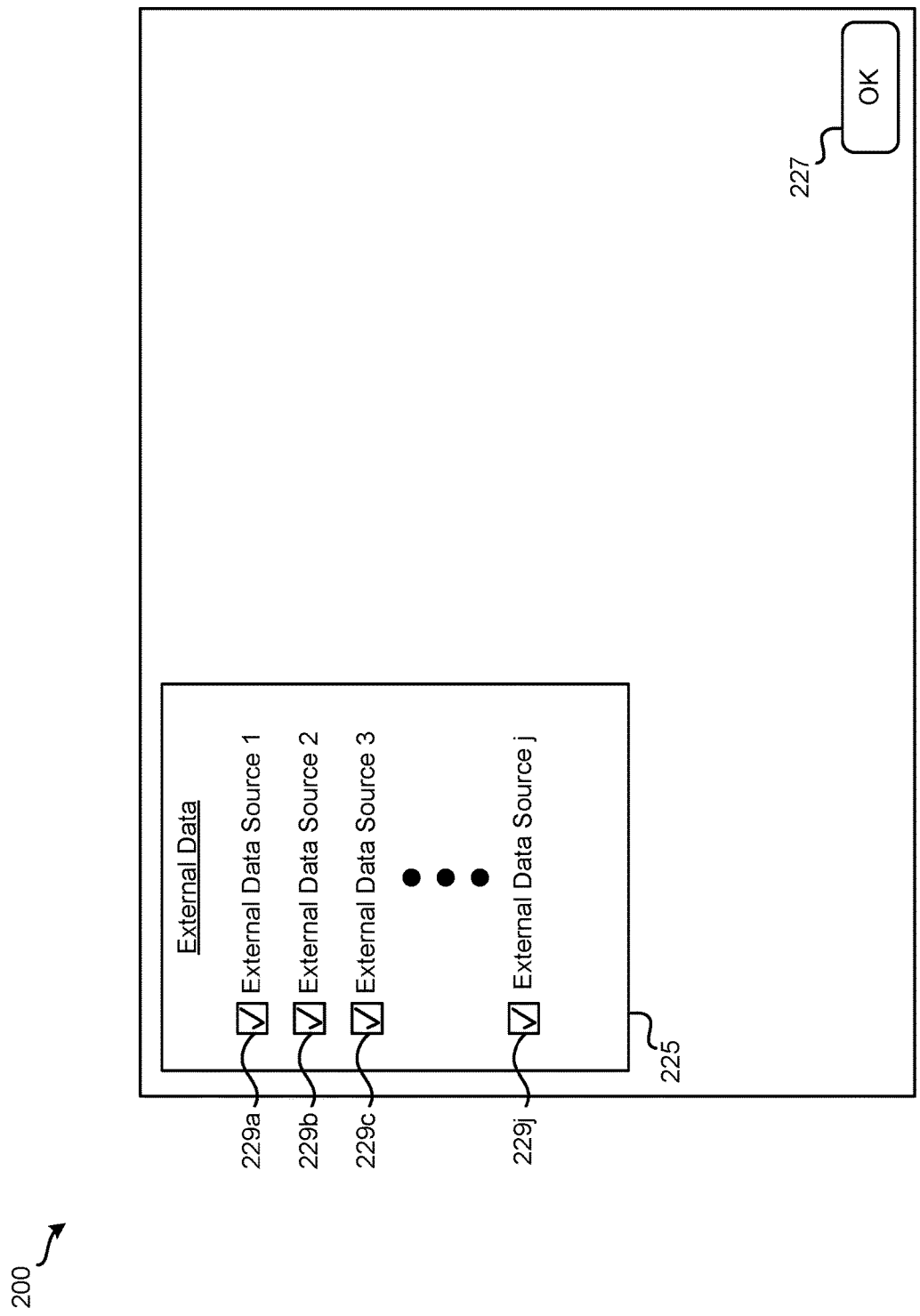

Referring now to FIG. 2B, FIG. 2B illustrates GUI 200 after the user selects UI item 210. As illustrated, GUI 200 in FIG. 2B includes external data configuration area 225 and selectable UI item 227. External data configuration area 225 includes selectable UI items 229*a-j* (e.g., checkboxes). A selection of a particular UI item 229 indicates that a corresponding type of data from one or more external data sources (e.g., external data sources 150*a-n*) will be included in the computational models. A non-selection of the particular UI item 229 indicates that the corresponding type of data will not be included in the computational models. For this example operation, four external data types are available: global disaster data, country risk data; incident data, and corporation information data; the user of client device 105 has selected the UI items 229 that correspond to these available external data types. As such, the corresponding types of external data will be included in the computational models. UI item 227, when selected, causes application 115 to save the external data configuration settings specified in external data configuration area 225 and then transition to the page of GUI 200 illustrated in FIG. 2A. In this example, the user of client device 105 selects UI item 227 after selecting UI items 229*a-j* in order to return to configuration menu 205 and then selects UI item 215 in configuration menu 205 to configure risk categories for the computational models.

Figure 2C:
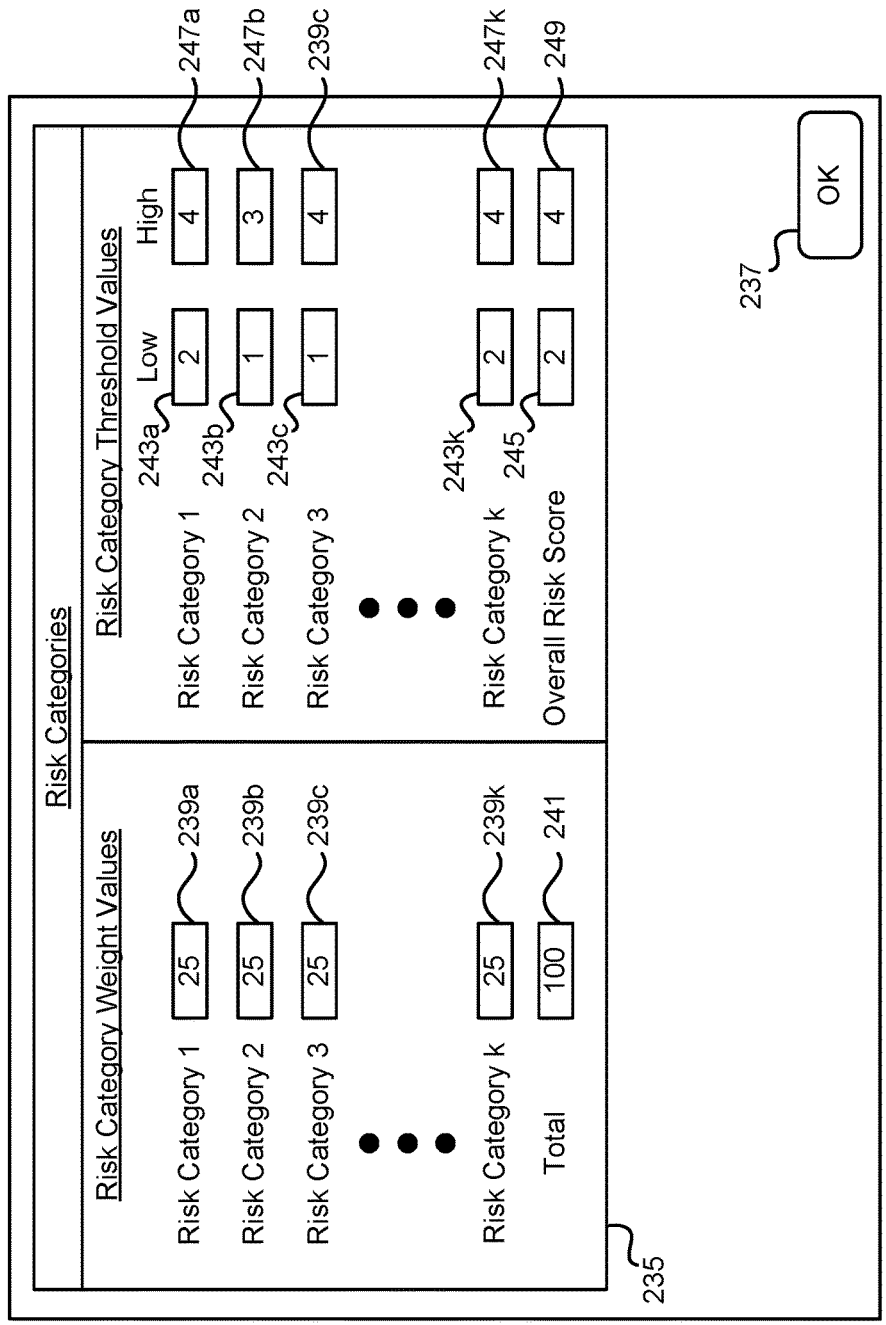

Referring now to FIG. 2C, FIG. 2C illustrates GUI 200 after the user selects UI item 215. As shown, GUI 200 in FIG. 2C includes risk category configuration area 235 and selectable UI item 237. Risk category configuration area 235 includes a section on the left side for specifying risk category weight values and a section on the right side for specifying risk category threshold values. Specifically, the section on the left side of risk category configuration area 235 includes UI controls 239*a-k* (e.g., data input fields) and UI control 241. Each UI control 239 is configured to receive numeric input that represents a percentage weight value for a corresponding risk category. UI control 241 is configured to display the sum of the numeric inputs provide in UI controls 239*a-k*. As shown, the section on the right side of risk category configuration area 235 includes UI controls 243*a-k* (e.g., data input fields), UI control 245 (e.g., a data input field), UI controls 247*a-k* (e.g., data input fields), and UI control 249 (e.g., a data input field). Each UI control 243 is configured to receive numeric input that represents a low threshold value for mapping a corresponding risk category risk score to a risk level (e.g., low or medium) for the risk category. UI control 245 is configured to receive numeric input that represents a low threshold value for mapping an overall risk score to an overall risk level (e.g., low or medium). Each UI control 247 is configured to receive numeric input that represents a high threshold value for mapping the corresponding risk category risk score to the risk level (e.g., medium or high) for the risk category. UI control 249 is configured to receive numeric input that represents a high threshold value for mapping an overall risk score to the overall risk level (e.g., low or medium).

In this example, four risk categories are available: a legal and regulatory risk category, a financial risk category, an environmental and social risk category, and an operational risk category. The user of client device 105 has specified a value of 25, which represents 25 percent, as the weight value for each risk category. For this example, risk scores generated by computational models are values between 0 and 5. As such, the user has specified the low threshold value and the high threshold value for risk category 1 as 2 and 4, respectively; the low threshold value and the high threshold value for risk category 2 as 1 and 3, respectively; the low threshold value and the high threshold value for risk category 3 as 1 and 4, respectively; the low threshold value and the high threshold value for risk category 4 as 1 and 4, respectively; and the low threshold value and the high threshold value for the overall risk score as 2 and 4, respectively. UI item 237, when selected, causes application 115 to save the risk category configuration settings specified in risk category configuration area 235 and then transition to the page of GUI 200 illustrated in FIG. 2A. In some embodiments, UI item 237 is selectable when the sum displayed in UI control 241 is equal to 100. For this example, the user of client device 105 selects UI item 237 after specifying data values for UI controls 239*a-k*, UI controls 243*a-k*, UI control 245, UI controls 247*a-k*, and UI control 249, as shown in FIG. 2C, in order to return to configuration menu 205 and then selects UI item 220 in configuration menu 205 to configure field definitions for the computational models.

Figure 2D:
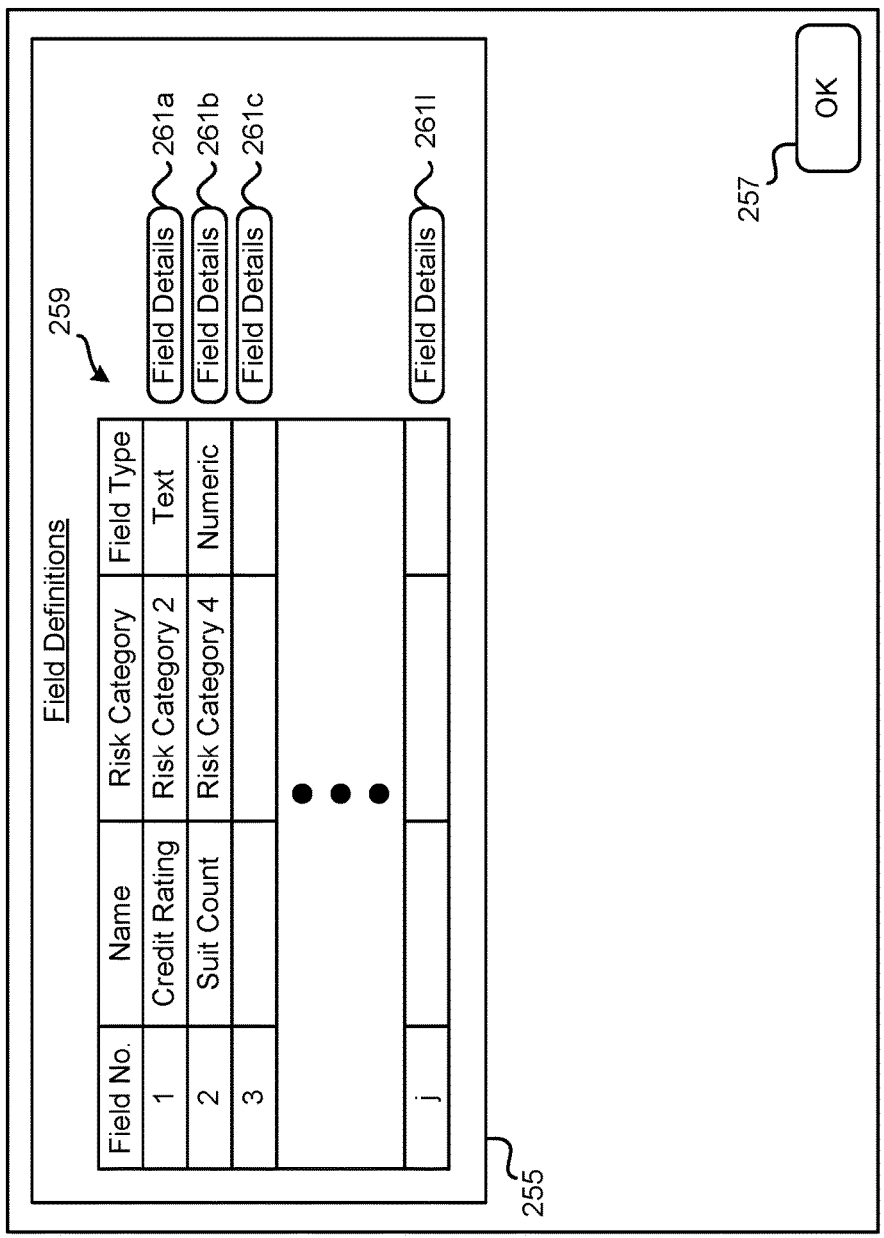

Referring now to FIG. 2D, FIG. 2D illustrates GUI 200 after the user selects UI item 220. As illustrated, GUI 200 in FIG. 2D includes field definition configuration area 255 and selectable UI item 257. Field definition configuration area 255 includes table 259 with j number of rows. Each row in table 259 represents a definition for a field. As shown, a row in table 259 has a column for specifying a name of the field, a column for specifying a risk category associated with the field, and column for specifying a field type of the field. Each row in table also has a corresponding selectable UI item 261 adjacent to it, which is configured to transition, when selected, to a page of GUI 200 for adding details for the corresponding field definition.

In this example, the user of client device 105 has specified two field definitions. In particular, the field definition for field number 1 has a name of Credit Rating, a risk category of Risk Category 2, and a field type of text. The field definition for field number 2 has a name of Suit Count, a risk category of Risk Category 4, and a field type of numeric. UI item 257, when selected, causes application 115 to save the field definition configuration settings specified in field definition configuration area 255 and then transition to the page of GUI 200 illustrated in FIG. 2A. For this example, the user of client device 105 selects UI item 261a after specifying data values for field definitions 1 and 2, as shown in FIG. 2D, in order to add details for field definition 1.

Figure 2E:
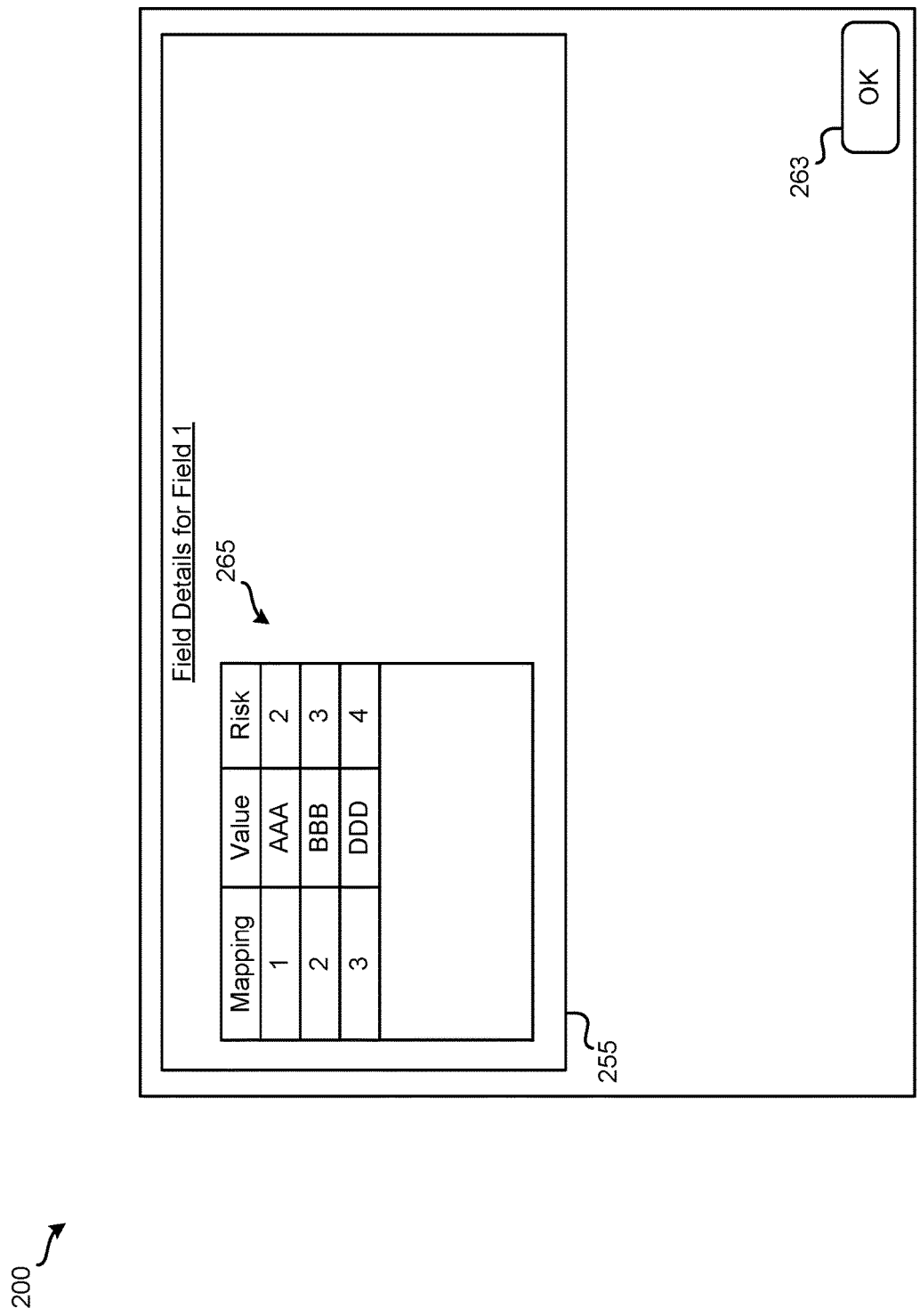

Referring now to FIG. 2E, FIG. 2E illustrates GUI 200 after the user selects UI item 261a. Specifically, FIG. 2E shows that field definition configuration area 255 of GUI 200 includes table 265 and GUI 200 includes selectable UI item 263. Since the field type specified for field definition 1 is a text field type, each row in table 265 represents a mapping between a text value and a risk value. A mapping may be added to table 265 via selection of a UI item (not shown). In this example, the user has added three mappings to table 265: a mapping between value AAA and risk value 2, a mapping between value BBB and risk value 3, and a mapping between value DDD and risk value 4. UI item 263, when selected, causes application 115 to save the field details for the corresponding field definition (field definition 1 in this example) and then transition to the page of GUI 200 illustrated in FIG. 2D. In this example, the user of client device 105 selects UI item 263 after adding the three mappings to table 265, as shown in FIG. 2E, in order to return to the page of GUI 200 illustrated in FIG. 2D and then selects UI item 261b in order to add details for field definition 2.

Figure 2F:
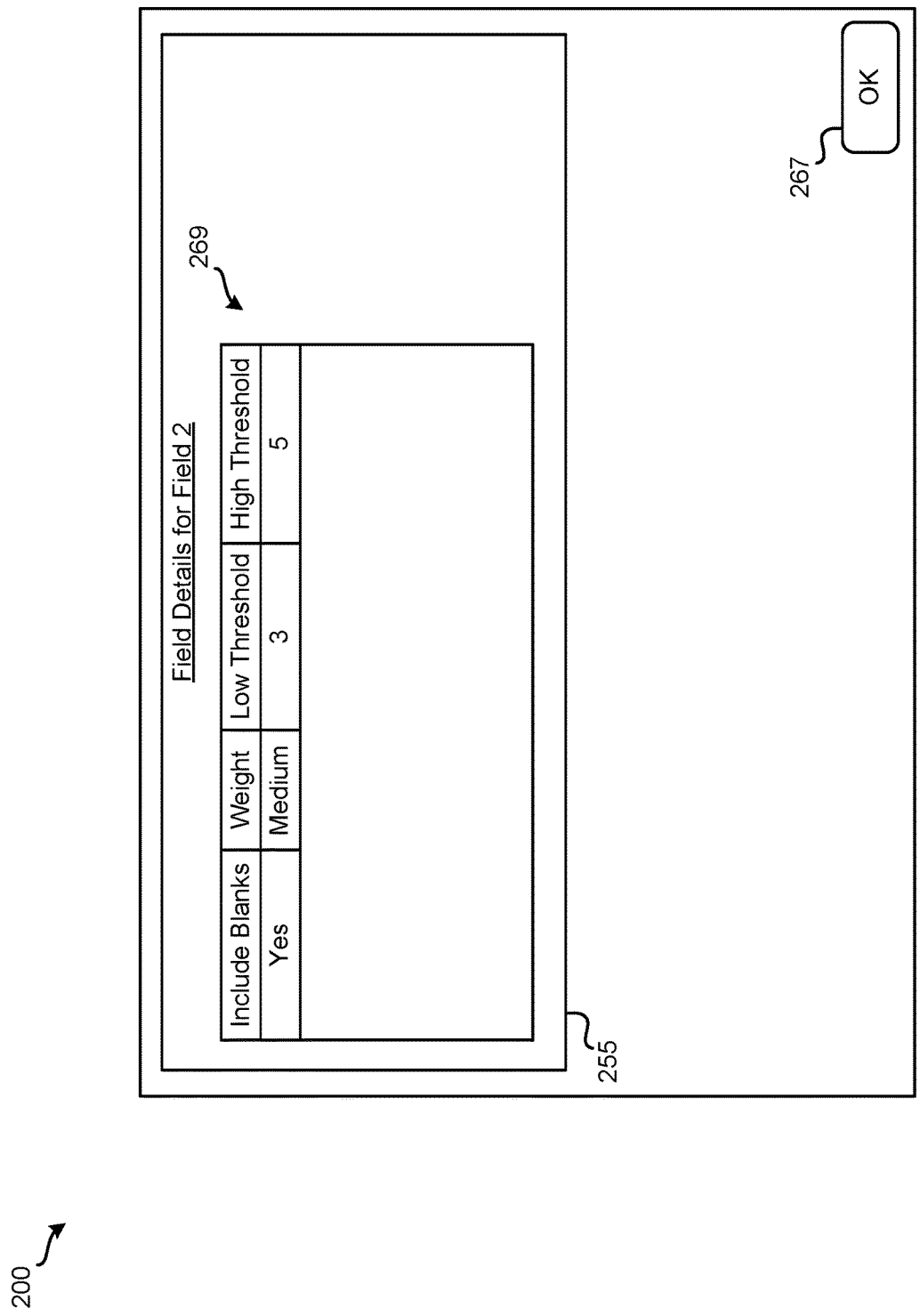

Referring now to FIG. 2F, FIG. 2F illustrates GUI 200 after the user selects UI item 261b. In particular, FIG. 2F shows that field definition configuration area 255 of GUI 200 includes table 266 and GUI 200 includes selectable UI item 267. Since the field type specified for field definition 2 is a numeric field type, the row in table 269 includes columns for specifying additional configuration settings for field definition 2. Specifically, the row in table 269A includes a column for specifying whether to include blank values in the field, a column for specifying a weight for the field (e.g., low, medium, or high), a column for specifying a low threshold value for mapping a value for the field to a risk level (e.g., low or medium), and a column for specifying a high threshold value for mapping the value for the field to the risk level (e.g., medium or medium). In this example, the user has specified to include blank values in the field, a weight of medium, a low threshold value of 3, and a high threshold value of 5. For this example, the user of client device 105 selects UI item 267 after specifying the values in table 269, as shown in FIG. 2F, in order to return to the page of GUI 200 illustrated in FIG. 2D. Next, the user selects UI item 257 in order to return to configuration menu 205 and then selects UI item 207 to send application 115 a request to generate computational models based on the configuration settings specified through the various configuration pages of GUI 200 described above.

When application 115 receives the request, application 115 sends the request and the configuration settings to model manager 120 for processing. To process the request, model manager 120 generates a set of computational models based on the configuration settings. As mentioned above, the set of computational models that model manager 120 generates may include different types of computational models for different risk categories. In this example, model manager 120 generates an entity computational model for a financial risk category, an entity computational model for an operational risk category, an entity computational model for an environmental and social risk category, and an entity computational model for a legal and regulatory risk category based on the equation (1) described above and the configuration settings. In addition, model manager 120 generates an incident computational model for a financial risk category, an incident computational model for an operational risk category, an incident computational model for an environmental and social risk category, and an incident computational model for a legal and regulatory risk category based on the equation (2) described above and the configuration settings. Next, model manager 120 retrieves entity data from entity data storage 140, enriches the entity data, and stores enriched entity data along with the set of computational models in models storage 135. To enrich the entity data, model manager 120 may request application 115 to prompt the user of client device 105 (e.g., via a GUI provided by application 115 to the user of client device 105) to provide data in fields defined according to field definitions for each entity associated with the user.

Figure 3:
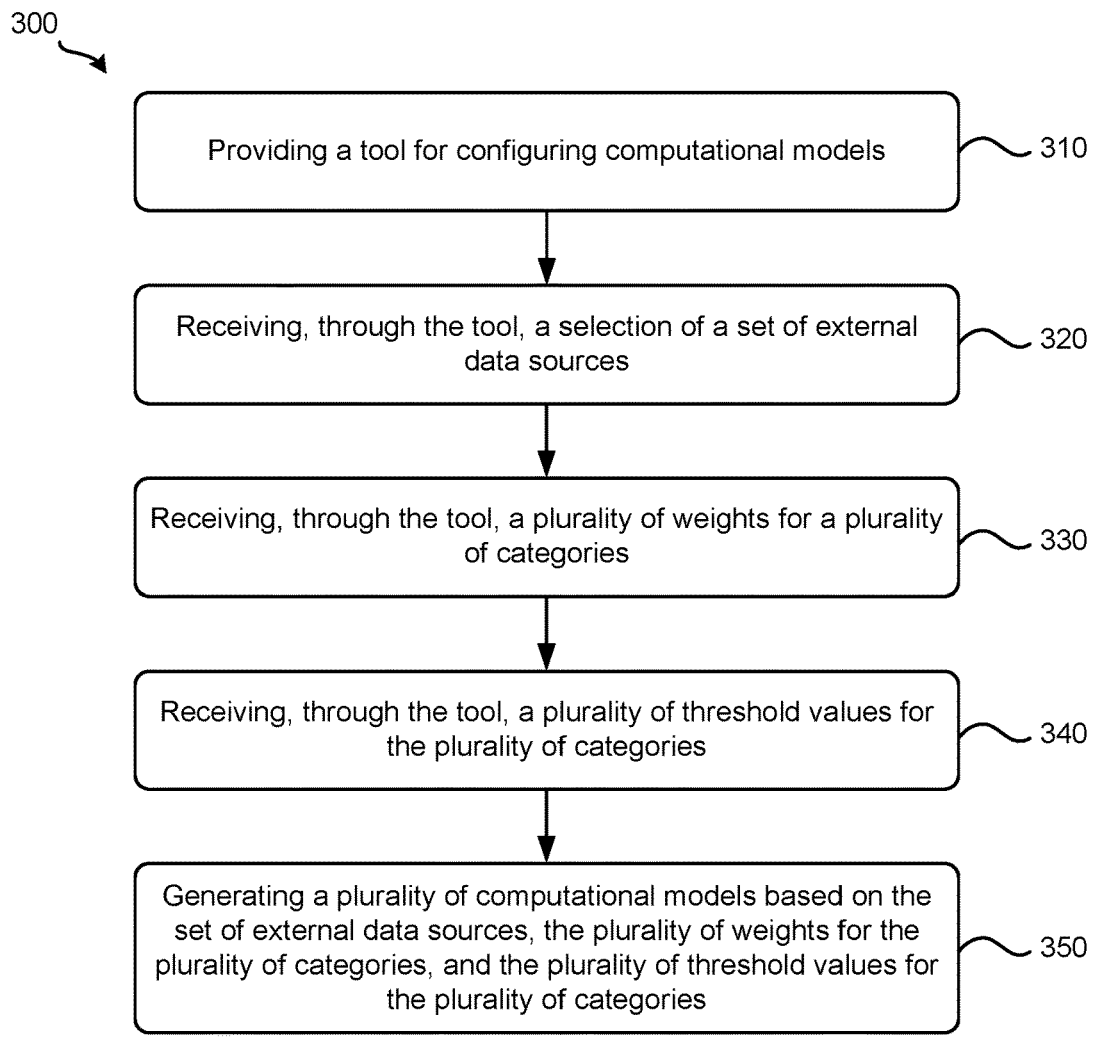
FIG. 3 illustrates a process for configuring computational models according to some embodiments.

FIG. 3 illustrates a process 300 for configuring computational models according to some embodiments. In some embodiments, computing system 110 performs process 300. Process 300 starts by providing, at 310, a tool for configuring computational models. Referring to FIGS. 1 and 2A-2F as an example, application 115 may receive a request for a computational model configuration tool from a user of client device 105. In response, application 115 provides the computational model configuration tool illustrated in GUI 200 of FIG. 2A.

Next, process receives, at 320, through the tool, a set of external data sources. Referring to FIGS. 1, 2A, and 2B as an example, application 115 may receive from a user of client device 105 a selection of UI item 210 in the GUI shown in FIG. 2A. In response, application 115 provides client device 105 with the GUI 200 illustrated in FIG. 2B. Then, application 115 may receive a selection of one or more external data sources displayed in external data configuration area 225.

Process 300 then receives, at 330, through the tool, a plurality of weights for a plurality of risk categories. Referring to FIGS. 1, 2A, and 2C as an example, application 115 may receive from a user of client device 105 a selection of UI item 215 in the GUI shown in FIG. 2A. In response, application 115 provides client device 105 with the GUI 200 illustrated in FIG. 2C. Application 115 may then receive a plurality of weights for a plurality of risk categories via UI controls 239a-k.

Next, process 300 receives, at 340, through the tool, a plurality of threshold values for the plurality of risk categories. Continuing with the example above, application 115 can further receive a plurality of threshold values for the plurality of risk categories via UI controls 243a-k and UI controls 247a-k. Finally, process 300 generates, at 350, a plurality of computational models based on the set of external data sources, the plurality of weights for the plurality of risk categories, and the plurality of threshold values for the plurality of risk categories. Referring to FIG. 1 as an example, application 115 can receive a request from client device 105 to generate computational models based on the configuration settings provided to application 115 via the computational model configuration tool. In response to the request, application 115 sends the request along with the configuration settings to model manager 120 for processing. When model manager 125 receives from application 115 configuration settings for computational models that were specified by a user (e.g., a user of client device 105) as well as a request to generate computational models, model manager 120 generates a set of computational models associated with the user of client device 105 based on the configuration settings and then stores the set of computational models in models storage 135. Model manager 120 may generate the set of computational models by retrieving entity data (e.g., entity data for entities associated with the user) from entity data storage 140, enriching the entity data, and storing the enriched entity data along with the set of computational models in models storage 135.

A first example risk information determination operation will now be described by reference to FIG. 1. The first example risk information determination operation starts by a user of client device 105 sending application 115 a request for risk information for an entity associated with the user. In response, application 115 sends the request to risk engine 125 for processing. When risk engine 125 receives the request, risk engine 125 sends model manager 120 a request for a set of computational models associated with the user and enriched entity data of the entity. Upon receiving the request, model manager 120 accesses models storage 135, retrieves the set of computational models associated with the user and enriched entity data for the entity associated with the user, and then sends the set of computational models and enriched entity data to risk engine 125. For this example, the configured set of computational models associated with the user includes an entity computational model for a legal and regulatory risk category. The enriched entity data for the entity includes a number of lawsuits currently open against the entity, which, in this example, is two lawsuits.

Next, risk engine 125 sends external data manager 130 a request for external data associated with the entity. Upon receiving the request, external data manager 130 accesses external data storage 145, retrieves a set of external data associated with the entity, and sends the set of external data to risk engine 125. In this example, external data storage 145 does not include any external data associated with the entity. As such, external data manager 130 sends risk engine 125 a message indicating so.

Based on the set of computational models and the enriched entity data, risk engine 125 then determines risk information for the entity. For this example, the risk information for the entity that risk engine 125 determines includes an overall risk score for the entity, an overall risk level for the entity, a risk score for the legal and regulatory risk category, and a risk level for the legal and regulatory risk category. To determine the risk score for the legal and regulatory risk category using the entity computational model, risk engine 125 uses equation (1) described above. For this example, the weight associated with the number of lawsuits against the entity is one. As such, the value of θ associated with the number of lawsuits against the entity is one. The amount of risk mitigated for the legal and regulatory risk category is none. In this example, the value of m may be between one and five, where a value of one represents no risk mitigated and a value of five represents the highest amount of risk mitigated. Thus, the value of m for this example is one.

In some embodiments, risk engine 125 determines the value b that is associated with an entity attribute based on the configuration settings for the computational models. The configuration settings for the number of lawsuits against the entity in this example is provided in the following Table 1:

TABLE 1

Configuration Settings for Suit Count Attribute

| Lower threshold | Upper threshold | Boost factor |
|---|---|---|
| −infinity | 0 | 1 |
| 1 | 4 | 2 |
| 5 | infinity | 3 |

Based on the configuration settings specified in Table 1, risk engine 125 determines that the boost factor for the number of lawsuits against the entity is two. Next, risk engine 125 normalizes the boost factor value to a value between one and five using a linear normalization method. Mappings between boost factor values and normalize values based on such a linear normalization method are provided in the following Table 2:

TABLE 2

Normalized Boost Factor Values for Suit Count Attribute

| Boost factor | Normalized Value |
|---|---|
| 1 | 1 |
| 2 | 3 |
| 3 | 5 |

Since the boost factor value in this example is two, risk engine 125 determines that the normalized value is three. Risk engine 125 uses this normalized boost factor value as the value for b for the number of lawsuits against the entity in equation (1). As such, risk engine 125 determines that the risk score for the legal and regulatory risk category as three based on the above values for b, θ, and m. Since there are no other computational models to consider in this example, risk engine 125 determines the overall risk score for the entity in this example to be the risk score for the legal and regulatory risk category, which is three in this example.

Next, risk engine 125 determines an overall risk level for the entity and the risk level for the legal and regulatory risk category. In some embodiments, risk engine 125 determines the overall risk level for the entity based on the overall risk score and configuration settings for the computational models. The configuration settings for the overall risk level in this example is provided in the following Table 3:

TABLE 3

Configuration Settings for Overall Risk Level

| Lower threshold | Upper threshold | Risk Level |
|---|---|---|
| 1 | 2 | Low |
| 2 | 4 | Medium |
| 4 |  | High |

Based on the configuration settings in specified Table 3, risk engine 125 determines the overall risk level for the entity to be a medium risk level. In some embodiments, risk engine 125 determines the risk level for the legal and regulatory risk category based on the risk score for the legal and regulatory risk category and configuration settings for the computational models. For this example, the configuration settings for the risk level for the legal and regulatory risk category is the same as that shown in Table 3 for the overall risk level. Thus, risk engine 125 determines the risk level for the legal and regulatory risk category to be a medium risk level. Risk engine 125 then sends application 115 the overall risk score, the overall risk level, the risk score for the legal and regulatory risk category, and the risk level for the legal and regulatory risk category. Upon receiving the risk information from risk engine 125, application 115 provides the risk information for the entity to client device 105.

A second example risk information determination operation will now be described by reference to FIG. 1. The second example risk information determination operation is similar to the first example risk information determination operation except the configured set of computational models associated with the user in this example includes the entity computational model for the legal and regulatory risk category described in the first example risk information determination operation as well as an entity computational model for a financial risk category. In addition, the enriched entity data for the entity also includes a financial evaluation rating of the entity. The financial evaluation rating may be a value between one and ten. In this example, the value of the financial evaluation rating of the entity is one.

Based on the set of computational models and the enriched entity data, risk engine 125 determines risk information for the entity. In this example, the risk information for the entity that risk engine 125 determines includes an overall risk score for the entity, an overall risk level for the entity, a risk score for the legal and regulatory risk category, a risk level for the legal and regulatory risk category, a risk score for the financial risk category, and a risk level for the financial risk category. Risk engine 125 determines the risk score for the legal and regulatory risk category and the risk level for the legal and regulatory risk category in the same manner described above in the first example risk information determination operation.

To determine the risk score for the financial risk category using the entity computational model, risk engine 125 also uses equation (1) mentioned above. In this example, the weight associated with the financial evaluation rating of the entity is one. Thus, the value of 0 associated with the financial evaluation rating of the entity is one. The amount of risk mitigated for the financial risk category is none. For this example, the value of m may be between one and five, where a value of one represents no risk mitigated and a value of five represents the highest amount of risk mitigated. As such, the value of m for this example is one.

As mentioned above, risk engine 125 determines the value b that is associated with an entity attribute based on the configuration settings for the computational models in some embodiments. The configuration settings for the financial evaluation rating of the entity for this example is provided in the following Table 4:

TABLE 4

Configuration Settings for Financial Evaluation Attribute

| Lower threshold | Upper threshold | Boost factor |
| --- | --- | --- |
| 1 | 3 | 1 |
| 4 | 7 | 2 |
| 8 | 10 | 3 |

Based on the configuration settings specified in Table 4, risk engine 125 determines that the boost factor for the financial evaluation rating of the entity is one. Risk engine 125 then normalizes the boost factor value to a value between one and five using a linear normalization method. Mappings between boost factor values and normalize values based on such a linear normalization method are provided in the following Table 5:

TABLE 5

Normalized Boost Factor Values for Financial Evaluation Attribute

| Boost factor | Normalized Value |
| --- | --- |
| 1 | 1 |
| 2 | 3 |
| 3 | 5 |

As the boost factor value in this example is one, risk engine 125 determines that the normalized value is one. Risk engine 125 uses this normalized boost factor value as the value for b for the financial evaluation rating of the entity in equation (1). Thus, risk engine 125 determines that the risk score for the financial risk category is one based on the above values for b, θ, and m. Risk engine 125 then determines the overall risk score for the entity in this example by calculating a weighted average of the risk score for the legal and regulatory risk category and the risk score for the financial risk category. In this example, the weight for the risk score for the legal and regulatory risk category is 60% and the weight for the risk score for the financial risk category is 40%. As such, risk engine 125 determines the overall risk score for the entity to be 2.2.

Next, risk engine 125 determines an overall risk level for the entity and risk levels for the legal and regulatory risk category and the financial risk category. As explained above, in some embodiments, risk engine 125 determines the overall risk level for the entity based on the overall risk score and configuration settings for the computational models. Based on the configuration settings specified in Table 3, risk engine 125 determines the overall risk level for the entity to be a medium risk level. Risk engine 125 determines the risk level for the legal and regulatory risk category in the same manner as that described in the first example risk information determination operation. Risk engine 125 determines the risk level for the financial risk category based on the risk score for the financial risk category and configuration settings for the computational models. In this example, the configuration settings for the risk level for the financial risk category is the same as that shown in Table 3 for the overall risk level. As such, risk engine 125 determines the risk level for the financial risk category to be a low risk level. Then, risk engine 125 sends application 115 the overall risk score, the overall risk level, the risk score for the legal and regulatory risk category, the risk level for the legal and regulatory risk category, the risk score for the financial risk category, and the risk level for the financial risk category. When application 115 receives the risk information from risk engine 125, application 115 provides the risk information for the entity to client device 105.

A third example risk information determination operation will now be described by reference to FIG. 1. The third example risk information determination operation is similar to the second example risk information determination operation except the configured set of computational models associated with the user for this example includes the entity computational model for the legal and regulatory risk category, the entity computational model for the financial risk category described in the second example risk information determination operation, and an incident computational model for the financial risk category. Additionally, the enriched entity data for the entity further includes bankruptcy incident data associated with the entity (e.g., a news article indicating the entity has filed for bankruptcy).

Based on the set of computational models and the enriched entity data, risk engine 125 determines risk information for the entity. For this example, the risk information for the entity that risk engine 125 determines is the same as the risk information determined in the second example risk information determination operation: an overall risk score for the entity, an overall risk level for the entity, a risk score for the legal and regulatory risk category, a risk level for the legal and regulatory risk category, a risk score for the financial risk category, and a risk level for the financial risk category.

To determine the risk score for the financial risk category, risk engine 125 determines a risk score for the financial risk category using the entity computational model and a risk score for the financial risk category using the incident computational model. Then, risk engine 125 selects the higher risk score between the two risk scores as the risk score for the financial risk category. Risk engine 125 determines the risk score for the financial risk category using the entity computational model in the same fashion as that described in the second example risk information determination operation.

To determine the risk score for the financial risk category using the incident computational model, risk engine 125 also uses equation (2) described above to determine the risk score for the financial risk category. In this example, the probability associated with the bankruptcy incident is 60% and the impact of the occurrence of the bankruptcy incident is 80%. The weight associated with the bankruptcy incident is one. As such, the value of boost associated with the number of lawsuits against the entity is one. In this example, the value of m may be between one and five, where a value of one represents no risk mitigated and a value of five represents the highest amount of risk mitigated. As such, the value of m for this example is one. Based on the above values for probability, impact, boost, and m, risk engine 125 determines that the risk score for the financial risk category using the incident computational model is 0.48. Risk engine 125 then normalizes the risk score on in a range between one and five by multiplying the risk score by four and adding one. The normalized risk score for the financial risk category using the incident computational model in this example is 2.92.

Risk engine 125 then determines the overall risk score for the entity. In this example, risk engine 125 selects the risk score of 2.4 determined for the financial risk category using the incident computational model since it is the higher risk score between the risk score determined for the financial risk category using the entity computational model and the risk score determined for the financial risk category using the incident computational model. Then, risk engine 125 determines the overall risk score for the entity by calculating a weighted average of the risk score for the legal and regulatory risk category and the selected risk score for the financial risk category. In this example, the weight for the risk score for the legal and regulatory risk category and the weight for the risk score for the financial risk category are the same as the ones in the second example risk information determination operation. Thus, risk engine 125 determines the overall risk score for the entity to be 2.76.

Risk engine 125 then determines an overall risk level for the entity and risk levels for the legal and regulatory risk category. Risk engine 125 determines the overall risk level and the risk level for the legal and regulatory risk category in the same manner as that described in the second example risk information determination operation. Risk engine 125 determines the risk level for the financial risk category based on the selected risk score for the financial risk category (i.e., the higher risk score between the risk score determined for the financial risk category using the entity computational model and the risk score determined for the financial risk category using the incident computational model) and configuration settings for the computational models. For this example, the configuration settings for the risk level for the financial risk category is the same as that shown in Table 3 for the overall risk level. As such, risk engine 125 determines the risk level for the financial risk category to be a medium risk level. Risk engine 125 then sends application 115 the overall risk score, the overall risk level, the risk score for the legal and regulatory risk category, the risk level for the legal and regulatory risk category, the risk score for the financial risk category, and the risk level for the financial risk category. Upon receiving the risk information from risk engine 125, application 115 provides the risk information for the entity to client device 105.

The example risk information determination operations described above determine risk information for an entity based on an entity computational model for a legal and regulatory risk category; based on an entity computational model for a legal and regulatory risk category and an entity computational model for a financial risk category; and based on an entity computational model for a legal and regulatory risk category, an entity computational model for a financial risk category, and an incident computational model for a financial risk category. One of ordinary skill in the art will appreciate that additional and/or different computational models for additional and/or different risk categories may be determined in the same or similar manner describe in the example risk information determination operations.

In addition, the example risk information determination operations described above use a linear normalization method to normalize boost factor values to a range of values between one and five. One of ordinary skill in the art will understand that different normalization techniques may be used in different embodiments. For instance, a Box-Cox Transform-based normalization technique may be used in some embodiments. Moreover, one of ordinary skill in the art will recognize that different boost factor values, different ranges of normalized values, and/or different configuration settings for computational models may be used in different embodiments.

Figure 4:
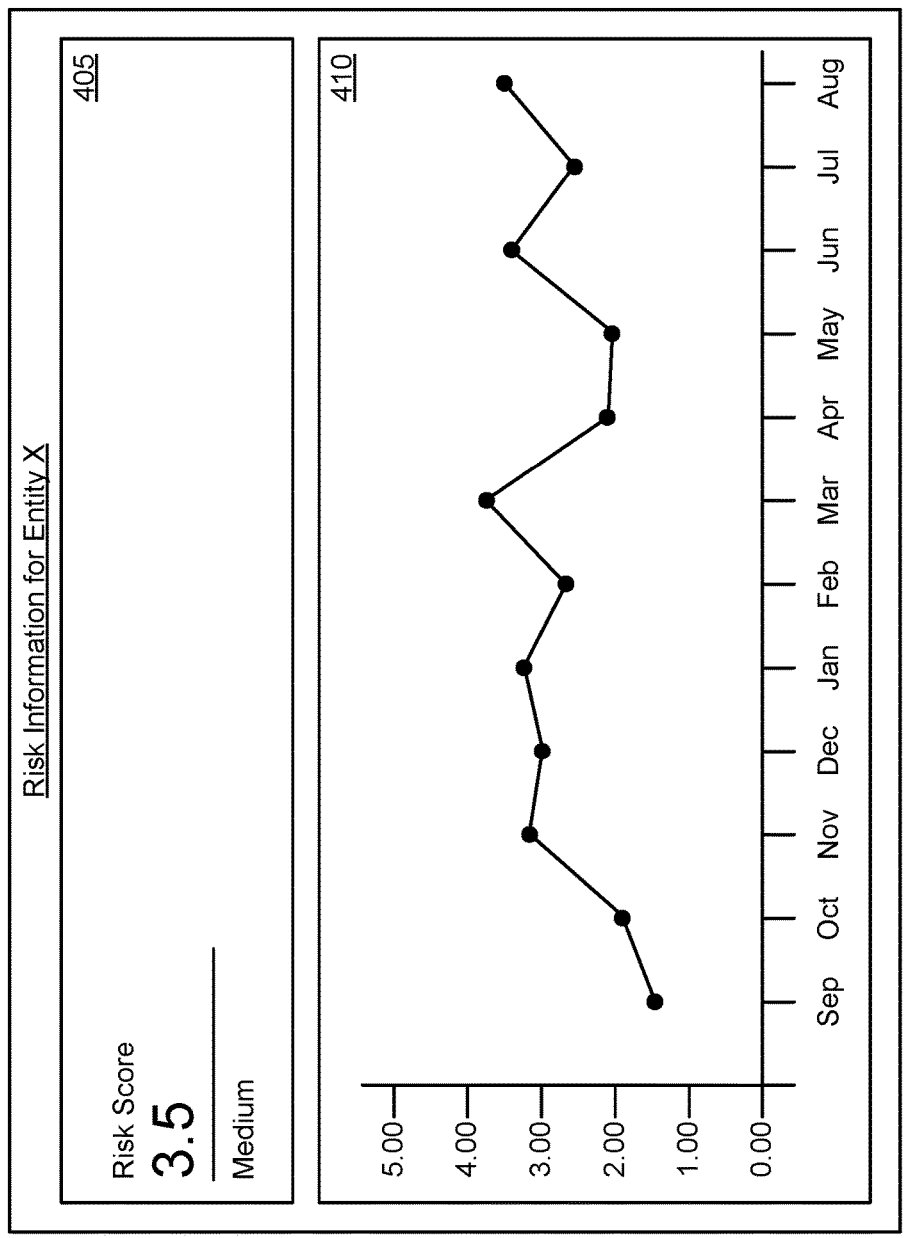
FIG. 4 illustrates a graphical user interface (GUI) for presenting risk information for an entity according to some embodiments.

In the example risk information determination operations described above, after application 115 receives risk information for an entity from risk engine 125, application 115 provides the risk information for the entity to client device 105. FIG. 4 illustrates a GUI 400 for presenting risk information for an entity according to some embodiments. In some embodiments, application 115 provides GUI 400 to a user of client device 105 in response to receiving a request for risk information for an entity X from the user of client device 105. For this example, the risk information for the entity X includes an overall risk score, an overall risk level, and a history of overall risk scores. As shown, GUI 400 includes display area 405 and display area 410. In this example, display area 405 provides an overall risk score (3.5 in this example) for an entity X and an overall risk level (medium in this example) for the entity X, which was provided to application 115 by risk engine 125. Display area 410 provides a line graph of the most recent twelve months of overall risk scores for the entity X.

Figure 5:
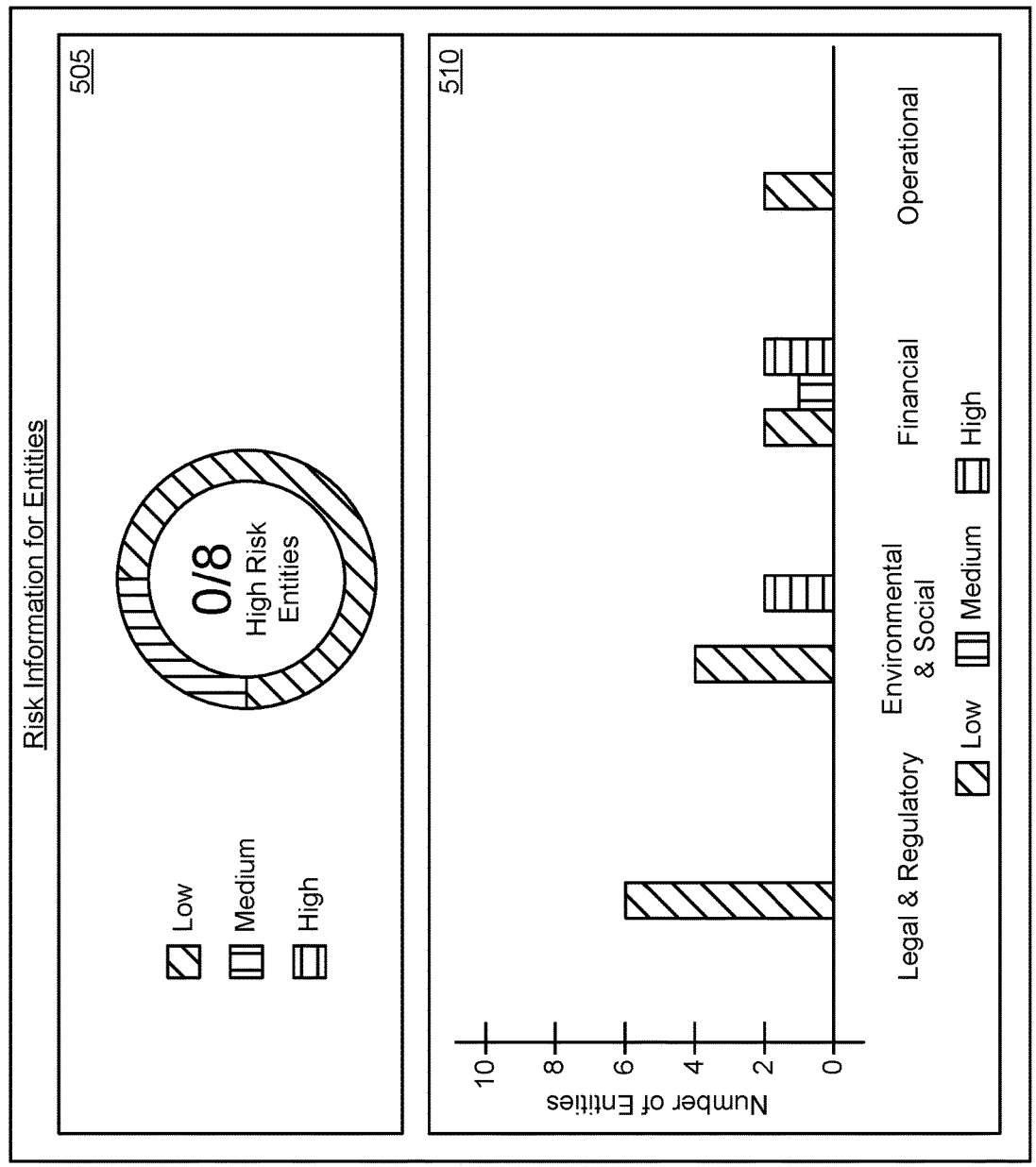
FIG. 5 illustrates a graphical user interface (GUI) for presenting risk information for several entities according to some embodiments.

FIG. 5 illustrates a GUI 500 for presenting risk information for several entities according to some embodiments. In some embodiments, application 115 provides GUI 500 to a user of client device 105 in response to receiving from the user of client device 105 a request for risk information for several entities (eight entities in this example) associated with the user. In this example, the risk information for the entities include an overall risk levels of the entities and risk category risk scores of the entities. Application 115 processes this risk information to provide the information shown in FIG. 5. As illustrated in FIG. 5, GUI 500 includes display area 505 and display area 510. For this example, display area 505 provides a donut chart that shows the portions of the entities that are low risk level entities (six in this example), medium risk level entities (two in this example), and high risk level entities (none in this example). Display area 510 provides a bar graph showing the number of entities that have low risk, medium risk, and high risk for the respective legal and regulatory, environmental and social, financial, and operational risk categories.

Figure 6:
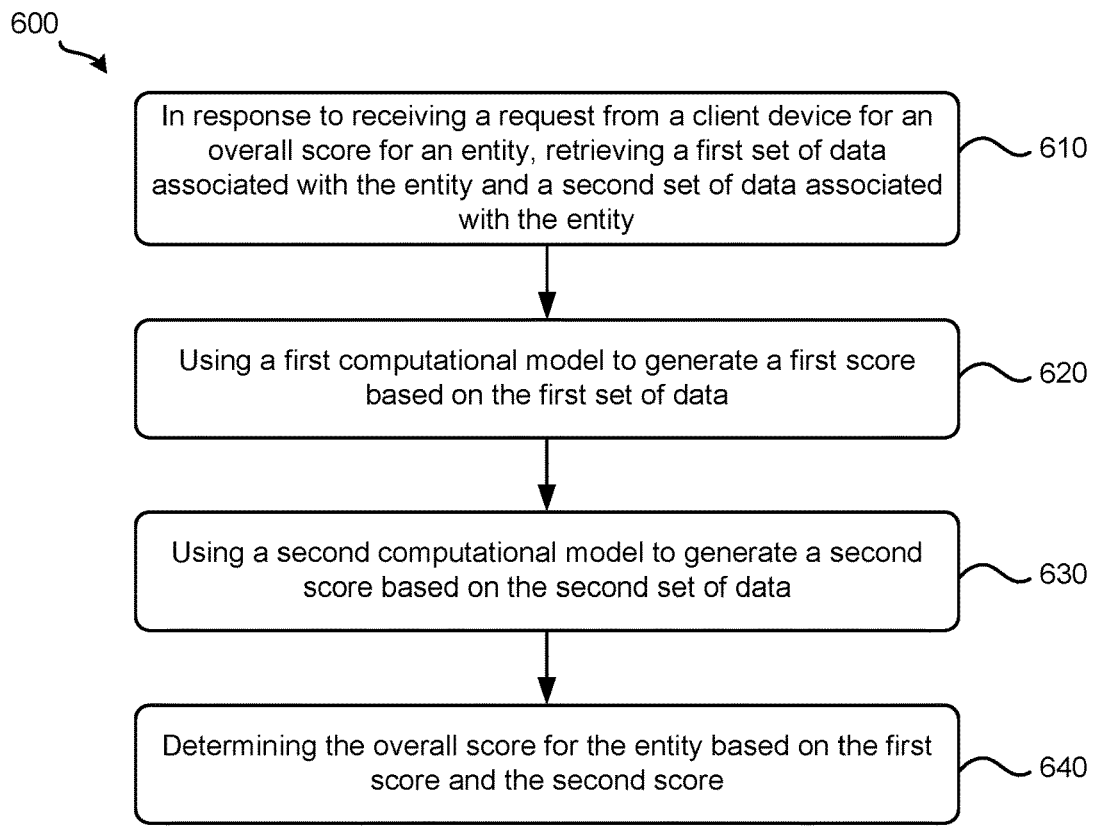
FIG. 6 illustrates a process for calculating an overall risk score according to some embodiments.

FIG. 6 illustrates a process 600 for calculating an overall risk score according to some embodiments. In some embodiments, computing system 110 performs process 600. Process 600 begins by retrieving, at 610, a first set of data associated with an entity and a second set of data associated with the entity in response to receiving a request from a client device for an overall risk score for an entity. Referring to FIG. 1 as an example. Application 115 may receive a request from a user of client device 105 for risk information for an entity that may include a risk score for the entity. In response, application 115 sends the request to risk engine 125 for processing. Risk engine 125. In response to the request, risk engine 125 sends model manager 120 a request for the set of computational models associated with the user and the enriched entity data of the entity (e.g., the first set of data associated with the entity). Risk engine 125 then sends external data manager 130 a request for external data associated with the entity (e.g., the second set of data associated with the entity).

Next, process 600 uses, at 620, a first computational model to generate a first risk score based on the set of data. Referring to FIG. 1 as an example, risk engine 125 may use an entity computational model to determine a risk score for a financial risk category based on a financial evaluation rating of the entity in the same way as that described above in the second example risk information determination operation. Process 600 then uses, at 630, a second computational model to generate a second risk score based on the second set of data. Referring to FIG. 1 as an example, risk engine 125 may use an incident computational model to determine a risk score for a financial risk category based on a bankruptcy incident in the same manner as that described above in the third example risk information determination operation.

Finally, process 600 determines, at 640, an overall risk score for the entity based on the first risk score and the second risk score. Referring to FIG. 1 as an example, risk engine 125 can determine the overall risk score for the entity in the same way as that described above in the third example risk information determination operation.

Figure 7:
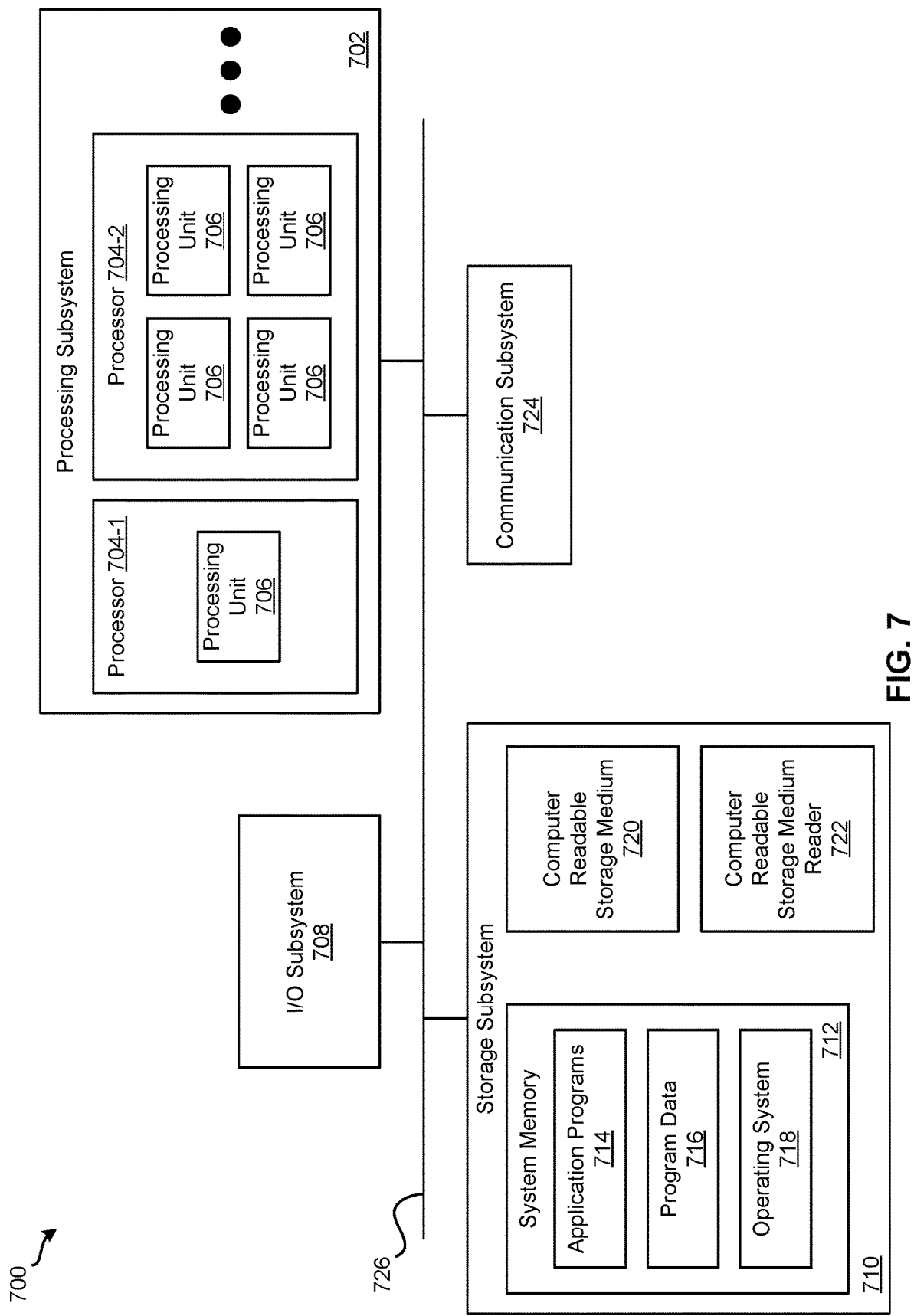
FIG. 7 illustrates an exemplary computer system, in which various embodiments may be implemented.

FIG. 7 illustrates an exemplary computer system 700 for implementing various embodiments described above. For example, computer system 700 may be used to implement client device 105 and computing system 110. Computer system 700 may be a desktop computer, a laptop, a server computer, or any other type of computer system or combination thereof. Some or all elements of application 115, model manager 120, risk engine 125, external data manager 130, or combinations thereof can be included or implemented in computer system 700. In addition, computer system 700 can implement many of the operations, methods, and/or processes described above (e.g., process 300 and process 600). As shown in FIG. 7, computer system 700 includes processing subsystem 702, which communicates, via bus subsystem 726, with input/output (I/O) subsystem 708, storage subsystem 710 and communication subsystem 724.

Bus subsystem 726 is configured to facilitate communication among the various components and subsystems of computer system 700. While bus subsystem 726 is illustrated in FIG. 7 as a single bus, one of ordinary skill in the art will understand that bus subsystem 726 may be implemented as multiple buses. Bus subsystem 726 may be any of several types of bus structures (e.g., a memory bus or memory controller, a peripheral bus, a local bus, etc.) using any of a variety of bus architectures. Examples of bus architectures may include an Industry Standard Architecture (ISA) bus, a Micro Channel Architecture (MCA) bus, an Enhanced ISA (EISA) bus, a Video Electronics Standards Association (VESA) local bus, a Peripheral Component Interconnect (PCI) bus, a Universal Serial Bus (USB), etc.

Processing subsystem 702, which can be implemented as one or more integrated circuits (e.g., a conventional microprocessor or microcontroller), controls the operation of computer system 700. Processing subsystem 702 may include one or more processors 704. Each processor 704 may include one processing unit 706 (e.g., a single core processor such as processor 704-1) or several processing units 706 (e.g., a multicore processor such as processor 704-2). In some embodiments, processors 704 of processing subsystem 702 may be implemented as independent processors while, in other embodiments, processors 704 of processing subsystem 702 may be implemented as multiple processors integrate into a single chip or multiple chips. Still, in some embodiments, processors 704 of processing subsystem 702 may be implemented as a combination of independent processors and multiple processors integrated into a single chip or multiple chips.

In some embodiments, processing subsystem 702 can execute a variety of programs or processes in response to program code and can maintain multiple concurrently executing programs or processes. At any given time, some or all of the program code to be executed can reside in processing subsystem 702 and/or in storage subsystem 710. Through suitable programming, processing subsystem 702 can provide various functionalities, such as the functionalities described above by reference to process 300, process 600, etc.

I/O subsystem 708 may include any number of user interface input devices and/or user interface output devices. User interface input devices may include a keyboard, pointing devices (e.g., a mouse, a trackball, etc.), a touchpad, a touch screen incorporated into a display, a scroll wheel, a click wheel, a dial, a button, a switch, a keypad, audio input devices with voice recognition systems, microphones, image/video capture devices (e.g., webcams, image scanners, barcode readers, etc.), motion sensing devices, gesture recognition devices, eye gesture (e.g., blinking) recognition devices, biometric input devices, and/or any other types of input devices.

User interface output devices may include visual output devices (e.g., a display subsystem, indicator lights, etc.), audio output devices (e.g., speakers, headphones, etc.), etc. Examples of a display subsystem may include a cathode ray tube (CRT), a flat-panel device (e.g., a liquid crystal display (LCD), a plasma display, etc.), a projection device, a touch screen, and/or any other types of devices and mechanisms for outputting information from computer system 700 to a user or another device (e.g., a printer).

As illustrated in FIG. 7, storage subsystem 710 includes system memory 712, computer-readable storage medium 720, and computer-readable storage medium reader 722. System memory 712 may be configured to store software in the form of program instructions that are loadable and executable by processing subsystem 702 as well as data generated during the execution of program instructions. In some embodiments, system memory 712 may include volatile memory (e.g., random access memory (RAM)) and/or non-volatile memory (e.g., read-only memory (ROM), programmable read-only memory (PROM), erasable programmable read-only memory (EPROM), electrically erasable programmable read-only memory (EEPROM), flash memory, etc.). System memory 712 may include different types of memory, such as static random access memory (SRAM) and/or dynamic random access memory (DRAM). System memory 712 may include a basic input/output system (BIOS), in some embodiments, that is configured to store basic routines to facilitate transferring information between elements within computer system 700 (e.g., during start-up). Such a BIOS may be stored in ROM (e.g., a ROM chip), flash memory, or any other type of memory that may be configured to store the BIOS.

As shown in FIG. 7, system memory 712 includes application programs 714 (e.g., application 115), program data 716, and operating system (OS) 718. OS 718 may be one of various versions of Microsoft Windows, Apple Mac OS, Apple OS X, Apple macOS, and/or Linux operating systems, a variety of commercially-available UNIX or UNIX-like operating systems (including without limitation the variety of GNU/Linux operating systems, the Google Chrome® OS, and the like) and/or mobile operating systems such as Apple iOS, Windows Phone, Windows Mobile, Android, BlackBerry OS, Blackberry 10, and Palm OS, WebOS operating systems.

Computer-readable storage medium 720 may be a non-transitory computer-readable medium configured to store software (e.g., programs, code modules, data constructs, instructions, etc.). Many of the components (e.g., application 115, model manager 120, risk engine 125, external data manager 130) and/or processes (e.g., process 300 and process 600) described above may be implemented as software that when executed by a processor or processing unit (e.g., a processor or processing unit of processing subsystem 702) performs the operations of such components and/or processes. Storage subsystem 710 may also store data used for, or generated during, the execution of the software.

Storage subsystem 710 may also include computer-readable storage medium reader 722 that is configured to communicate with computer-readable storage medium 720. Together and, optionally, in combination with system memory 712, computer-readable storage medium 720 may comprehensively represent remote, local, fixed, and/or removable storage devices plus storage media for temporarily and/or more permanently containing, storing, transmitting, and retrieving computer-readable information.

Computer-readable storage medium 720 may be any appropriate media known or used in the art, including storage media such as volatile, non-volatile, removable, non-removable media implemented in any method or technology for storage and/or transmission of information. Examples of such storage media includes RAM, ROM, EEPROM, flash memory or other memory technology, compact disc read-only memory (CD-ROM), digital versatile disk (DVD), Blu-ray Disc (BD), magnetic cassettes, magnetic tape, magnetic disk storage (e.g., hard disk drives), Zip drives, solid-state drives (SSD), flash memory card (e.g., secure digital (SD) cards, CompactFlash cards, etc.), USB flash drives, or any other type of computer-readable storage media or device.

Communication subsystem 724 serves as an interface for receiving data from, and transmitting data to, other devices, computer systems, and networks. For example, communication subsystem 724 may allow computer system 700 to connect to one or more devices via a network (e.g., a personal area network (PAN), a local area network (LAN), a storage area network (SAN), a campus area network (CAN), a metropolitan area network (MAN), a wide area network (WAN), a global area network (GAN), an intranet, the Internet, a network of any number of different types of networks, etc.). Communication subsystem 724 can include any number of different communication components. Examples of such components may include radio frequency (RF) transceiver components for accessing wireless voice and/or data networks (e.g., using cellular technologies such as 2G, 3G, 4G, 5G, etc., wireless data technologies such as Wi-Fi, Bluetooth, ZigBee, etc., or any combination thereof), global positioning system (GPS) receiver components, and/or other components. In some embodiments, communication subsystem 724 may provide components configured for wired communication (e.g., Ethernet) in addition to or instead of components configured for wireless communication.

One of ordinary skill in the art will realize that the architecture shown in FIG. 7 is only an example architecture of computer system 700, and that computer system 700 may have additional or fewer components than shown, or a different configuration of components. The various components shown in FIG. 7 may be implemented in hardware, software, firmware or any combination thereof, including one or more signal processing and/or application specific integrated circuits.

Figure 8:
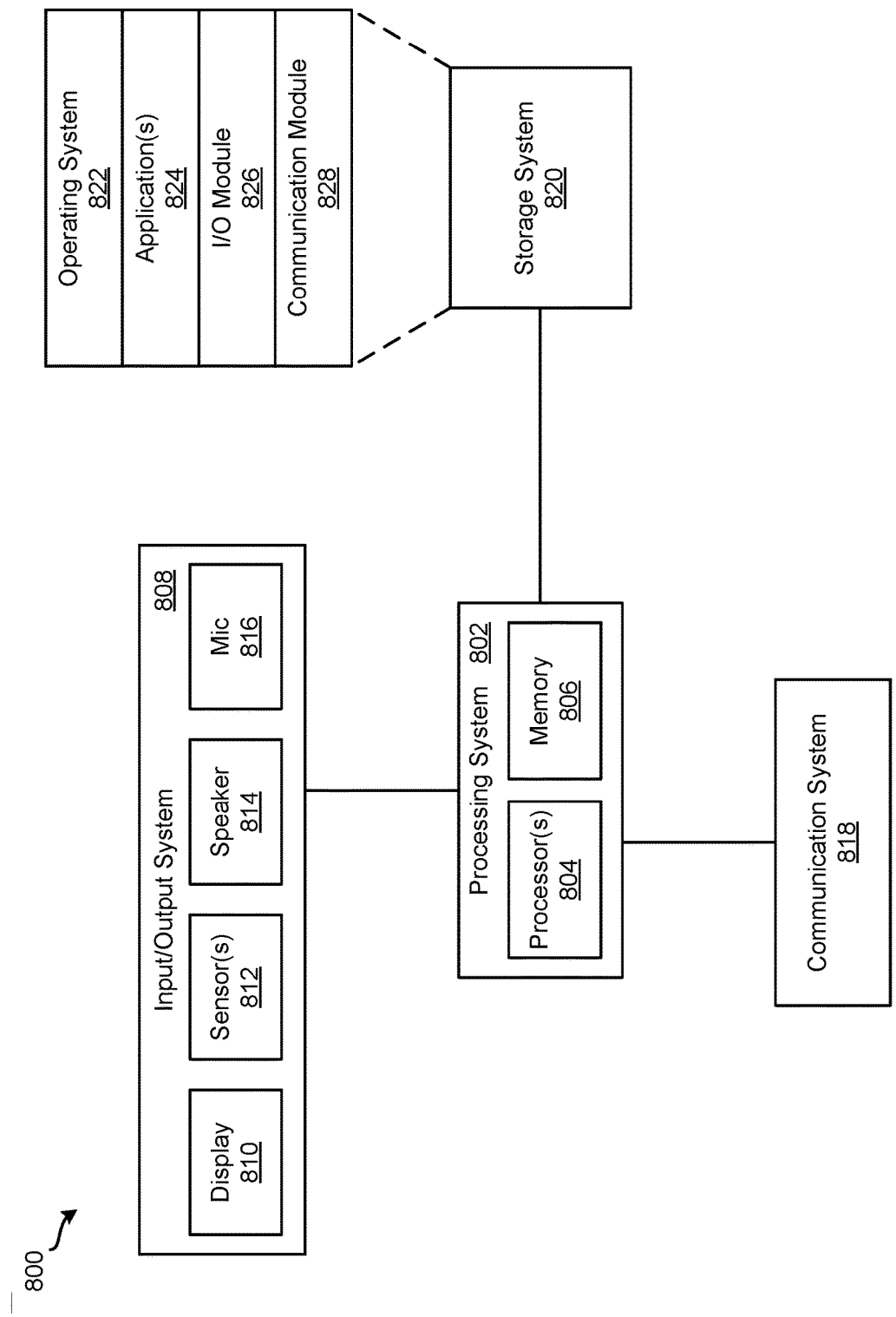
FIG. 8 illustrates an exemplary computing device, in which various embodiments may be implemented.

FIG. 8 illustrates an exemplary computing device 800 for implementing various embodiments described above. For example, computing device 800 may be used to implement client device 105. Computing device 800 may be a cellphone, a smartphone, a wearable device, an activity tracker or manager, a tablet, a personal digital assistant (PDA), a media player, or any other type of mobile computing device or combination thereof. As shown in FIG. 8, computing device 800 includes processing system 802, input/output (I/O) system 808, communication system 818, and storage system 820. These components may be coupled by one or more communication buses or signal lines.

Processing system 802, which can be implemented as one or more integrated circuits (e.g., a conventional microprocessor or microcontroller), controls the operation of computing device 800. As shown, processing system 802 includes one or more processors 804 and memory 806. Processors 804 are configured to run or execute various software and/or sets of instructions stored in memory 806 to perform various functions for computing device 800 and to process data.

Each processor of processors 804 may include one processing unit (e.g., a single core processor) or several processing units (e.g., a multicore processor). In some embodiments, processors 804 of processing system 802 may be implemented as independent processors while, in other embodiments, processors 804 of processing system 802 may be implemented as multiple processors integrate into a single chip. Still, in some embodiments, processors 804 of processing system 802 may be implemented as a combination of independent processors and multiple processors integrated into a single chip.

Memory 806 may be configured to receive and store software (e.g., operating system 822, applications 824, I/O module 826, communication module 828, etc. from storage system 820) in the form of program instructions that are loadable and executable by processors 804 as well as data generated during the execution of program instructions. In some embodiments, memory 806 may include volatile memory (e.g., random access memory (RAM)), non-volatile memory (e.g., read-only memory (ROM), programmable read-only memory (PROM), erasable programmable read-only memory (EPROM), electrically erasable programmable read-only memory (EEPROM), flash memory, etc.), or a combination thereof.

I/O system 808 is responsible for receiving input through various components and providing output through various components. As shown for this example, I/O system 808 includes display 810, one or more sensors 812, speaker 814, and microphone 816. Display 810 is configured to output visual information (e.g., a graphical user interface (GUI) generated and/or rendered by processors 804). In some embodiments, display 810 is a touch screen that is configured to also receive touch-based input. Display 810 may be implemented using liquid crystal display (LCD) technology, light-emitting diode (LED) technology, organic LED (OLED) technology, organic electro luminescence (OEL) technology, or any other type of display technologies. Sensors 812 may include any number of different types of sensors for measuring a physical quantity (e.g., temperature, force, pressure, acceleration, orientation, light, radiation, etc.). Speaker 814 is configured to output audio information and microphone 816 is configured to receive audio input. One of ordinary skill in the art will appreciate that I/O system 808 may include any number of additional, fewer, and/or different components. For instance, I/O system 808 may include a keypad or keyboard for receiving input, a port for transmitting data, receiving data and/or power, and/or communicating with another device or component, an image capture component for capturing photos and/or videos, etc.

Communication system 818 serves as an interface for receiving data from, and transmitting data to, other devices, computer systems, and networks. For example, communication system 818 may allow computing device 800 to connect to one or more devices via a network (e.g., a personal area network (PAN), a local area network (LAN), a storage area network (SAN), a campus area network (CAN), a metropolitan area network (MAN), a wide area network (WAN), a global area network (GAN), an intranet, the Internet, a network of any number of different types of networks, etc.). Communication system 818 can include any number of different communication components. Examples of such components may include radio frequency (RF) transceiver components for accessing wireless voice and/or data networks (e.g., using cellular technologies such as 2G, 3G, 4G, 5G, etc., wireless data technologies such as Wi-Fi, Bluetooth, ZigBee, etc., or any combination thereof), global positioning system (GPS) receiver components, and/or other components. In some embodiments, communication system 818 may provide components configured for wired communication (e.g., Ethernet) in addition to or instead of components configured for wireless communication.

Storage system 820 handles the storage and management of data for computing device 800. Storage system 820 may be implemented by one or more non-transitory machine-readable mediums that are configured to store software (e.g., programs, code modules, data constructs, instructions, etc.) and store data used for, or generated during, the execution of the software.

In this example, storage system 820 includes operating system 822, one or more applications 824, I/O module 826, and communication module 828. Operating system 822 includes various procedures, sets of instructions, software components and/or drivers for controlling and managing general system tasks (e.g., memory management, storage device control, power management, etc.) and facilitates communication between various hardware and software components. Operating system 822 may be one of various versions of Microsoft Windows, Apple Mac OS, Apple OS X, Apple macOS, and/or Linux operating systems, a variety of commercially-available UNIX or UNIX-like operating systems (including without limitation the variety of GNU/Linux operating systems, the Google Chrome® OS, and the like) and/or mobile operating systems such as Apple iOS, Windows Phone, Windows Mobile, Android, BlackBerry OS, Blackberry 10, and Palm OS, WebOS operating systems.

Applications 824 can include any number of different applications installed on computing device 800. Examples of such applications may include a browser application, an address book application, a contact list application, an email application, an instant messaging application, a word processing application, JAVA-enabled applications, an encryption application, a digital rights management application, a voice recognition application, location determination application, a mapping application, a music player application, etc.

I/O module 826 manages information received via input components (e.g., display 810, sensors 812, and microphone 816) and information to be outputted via output components (e.g., display 810 and speaker 814). Communication module 828 facilitates communication with other devices via communication system 818 and includes various software components for handling data received from communication system 818.

One of ordinary skill in the art will realize that the architecture shown in FIG. 8 is only an example architecture of computing device 800, and that computing device 800 may have additional or fewer components than shown, or a different configuration of components. The various components shown in FIG. 8 may be implemented in hardware, software, firmware or any combination thereof, including one or more signal processing and/or application specific integrated circuits.

Figure 9:
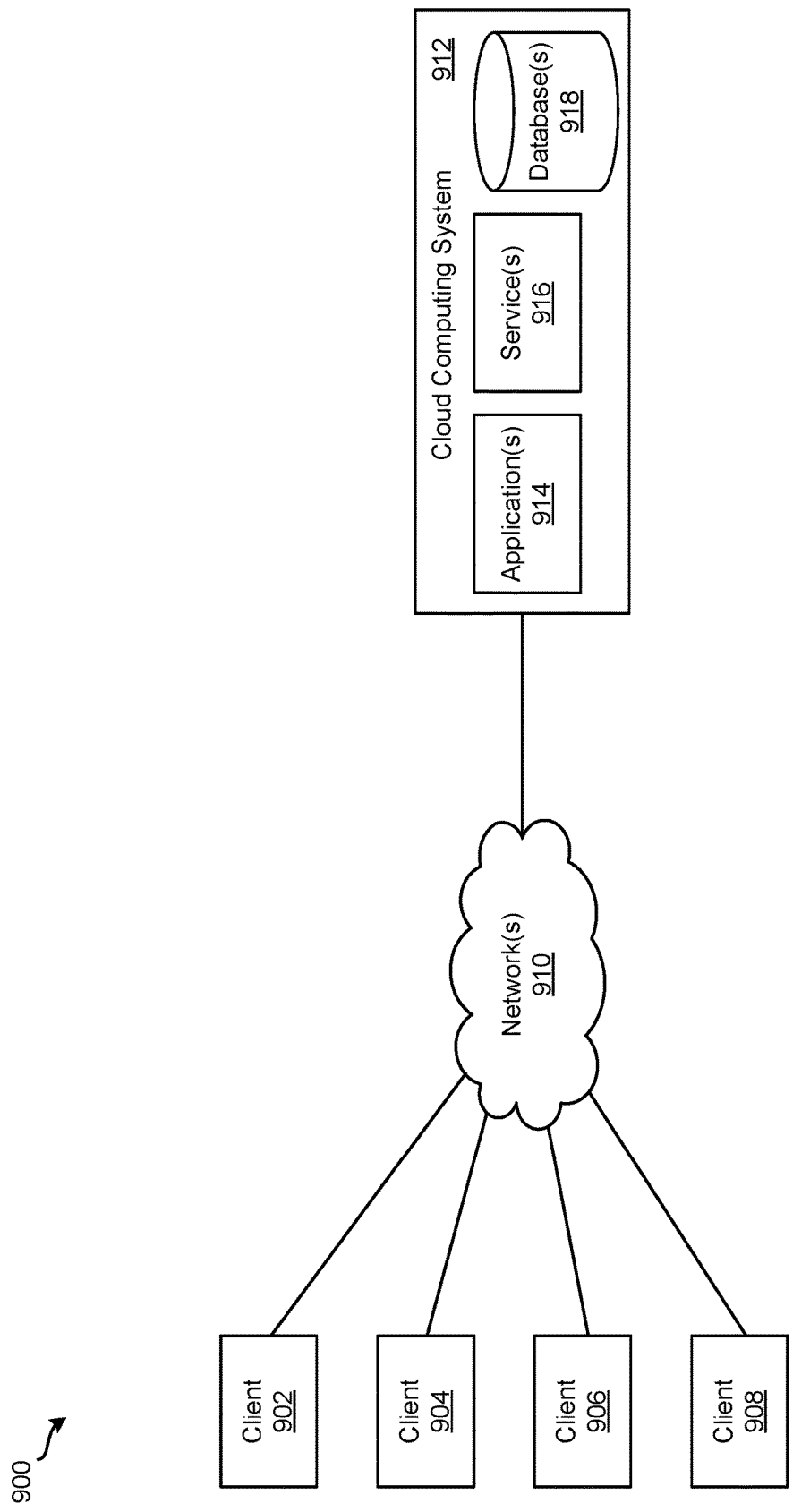
FIG. 9 illustrates system for implementing various embodiments described above.

FIG. 9 illustrates an exemplary system 900 for implementing various embodiments described above. For example, cloud computing system 912 of system 900 may be used to implement computing system 110 and one of client devices 902-908 may be used to implement client device 105. As shown, system 900 includes client devices 902-908, one or more networks 910, and cloud computing system 912. Cloud computing system 912 is configured to provide resources and data to client devices 902-908 via networks 910. In some embodiments, cloud computing system 900 provides resources to any number of different users (e.g., customers, tenants, organizations, etc.). Cloud computing system 912 may be implemented by one or more computer systems (e.g., servers), virtual machines operating on a computer system, or a combination thereof.

As shown, cloud computing system 912 includes one or more applications 914, one or more services 916, and one or more databases 918. Cloud computing system 900 may provide applications 914, services 916, and databases 918 to any number of different customers in a self-service, subscription-based, elastically scalable, reliable, highly available, and secure manner.

In some embodiments, cloud computing system 900 may be adapted to automatically provision, manage, and track a customer's subscriptions to services offered by cloud computing system 900. Cloud computing system 900 may provide cloud services via different deployment models. For example, cloud services may be provided under a public cloud model in which cloud computing system 900 is owned by an organization selling cloud services and the cloud services are made available to the general public or different industry enterprises. As another example, cloud services may be provided under a private cloud model in which cloud computing system 900 is operated solely for a single organization and may provide cloud services for one or more entities within the organization. The cloud services may also be provided under a community cloud model in which cloud computing system 900 and the cloud services provided by cloud computing system 900 are shared by several organizations in a related community. The cloud services may also be provided under a hybrid cloud model, which is a combination of two or more of the aforementioned different models.

In some instances, any one of applications 914, services 916, and databases 918 made available to client devices 902-908 via networks 910 from cloud computing system 900 is referred to as a "cloud service." Typically, servers and systems that make up cloud computing system 900 are different from the on-premises servers and systems of a customer. For example, cloud computing system 900 may host an application and a user of one of client devices 902-908 may order and use the application via networks 910.

Applications 914 may include software applications that are configured to execute on cloud computing system 912 (e.g., a computer system or a virtual machine operating on a computer system) and be accessed, controlled, managed, etc. via client devices 902-908. In some embodiments, applications 914 may include server applications and/or mid-tier applications (e.g., HTTP (hypertext transport protocol) server applications, FTP (file transfer protocol) server applications, CGI (common gateway interface) server applications, JAVA server applications, etc.). Services 916 are software components, modules, application, etc. that are configured to execute on cloud computing system 912 and provide functionalities to client devices 902-908 via networks 910. Services 916 may be web-based services or on-demand cloud services.

Databases 918 are configured to store and/or manage data that is accessed by applications 914, services 916, and/or client devices 902-908. For instance, storages 135-145 may be stored in databases 918. Databases 918 may reside on a non-transitory storage medium local to (and/or resident in) cloud computing system 912, in a storage-area network (SAN), on a non-transitory storage medium local located remotely from cloud computing system 912. In some embodiments, databases 918 may include relational databases that are managed by a relational database management system (RDBMS). Databases 918 may be a column-oriented databases, row-oriented databases, or a combination thereof. In some embodiments, some or all of databases 918 are in-memory databases. That is, in some such embodiments, data for databases 918 are stored and managed in memory (e.g., random access memory (RAM)).

Client devices 902-908 are configured to execute and operate a client application (e.g., a web browser, a proprietary client application, etc.) that communicates with applications 914, services 916, and/or databases 918 via networks 910. This way, client devices 902-908 may access the various functionalities provided by applications 914, services 916, and databases 918 while applications 914, services 916, and databases 918 are operating (e.g., hosted) on cloud computing system 900. Client devices 902-908 may be computer system 1000 or computing device 1100, as described above by reference to FIGS. 10 and 11, respectively. Although system 900 is shown with four client devices, any number of client devices may be supported.

Networks 910 may be any type of network configured to facilitate data communications among client devices 902-908 and cloud computing system 912 using any of a variety of network protocols. Networks 910 may be a personal area network (PAN), a local area network (LAN), a storage area network (SAN), a campus area network (CAN), a metropolitan area network (MAN), a wide area network (WAN), a global area network (GAN), an intranet, the Internet, a network of any number of different types of networks, etc.

The above description illustrates various embodiments of the present invention along with examples of how aspects of the present invention may be implemented. The above examples and embodiments should not be deemed to be the only embodiments, and are presented to illustrate the flexibility and advantages of the present invention as defined by the following claims. Based on the above disclosure and the following claims, other arrangements, embodiments, implementations and equivalents will be evident to those skilled in the art and may be employed without departing from the spirit and scope of the invention as defined by the claims.

What is claimed is:

1. A non-transitory machine-readable medium storing a program executable by at least one processing unit of a device, the program comprising sets of instructions for:
    providing a client device a tool for configuring computational models;
    receiving, from the client device and through the tool, a selection of a set of different external data sources;
    receiving, from the client device and through the tool, a plurality of weight values for a plurality of different categories;
    receiving, from the client device and through the tool, a plurality of threshold values for the plurality of different categories;
    generating a plurality of different types of computational models based on the set of different external data sources, the plurality of weight values for the plurality of different categories, and the plurality of threshold values for the plurality of different categories, wherein each computational model in the plurality of different types of computational models is configured to generate a score associated with a category in the plurality different of categories;
receiving, from the client device, a request for an overall score for an entity;
using the plurality of different types of computational models to generate a plurality of scores for the entity; and
determining the overall score for the entity based on the plurality of scores.

2. The non-transitory machine-readable medium of claim 1, wherein the program further comprises a set of instructions for receiving, from the client device and through the tool, a set of field definitions, wherein generating the plurality of different types of computational models is further based on the set of field definitions.

3. The non-transitory machine-readable medium of claim 2, wherein a field definition in the set of field definitions specifies a name, a category in the plurality of different categories, and a field type.

4. The non-transitory machine-readable medium of claim 3, wherein the field definition specifies the field type as a text field type, wherein the field definition further specifies a set of mappings between a set of text values and a set of values.

5. The non-transitory machine-readable medium of claim 3, wherein the field definition specifies the field type as a numeric field type, wherein the field definition further specifies a weight, a low threshold value, and a high threshold value.

6. The non-transitory machine-readable medium of claim 1, wherein the plurality of threshold values for the plurality of different categories is a first plurality of threshold values, wherein the program further comprises a set of instructions for receiving, from the client device and through the tool, a second plurality of threshold values for the plurality of different categories, wherein generating the plurality of different types of computational models is further based on the second plurality of threshold values for the plurality of different categories.

7. The non-transitory machine-readable medium of claim 1, wherein the program further comprises a set of instructions for receiving, from the client device and through the tool, a first threshold value for an overall score and a second threshold value for the overall score, wherein generating the plurality of different types of computational models is further based on the first threshold value for the overall score and the second threshold value for the overall score.

8. A method comprising:
providing a client device a tool for configuring computational models;
receiving, from the client device and through the tool, a selection of a set of different external data sources;
receiving, from the client device and through the tool, a plurality of weight values for a plurality of different categories;
receiving, from the client device and through the tool, a plurality of threshold values for the plurality of different categories;
generating a plurality of different types of computational models based on the set of different external data sources, the plurality of weight values for the plurality of different categories, and the plurality of threshold values for the plurality of different categories, wherein each computational model in the plurality of different types of computational models is configured to generate a score associated with a category in the plurality of different categories;
receiving, from the client device, a request for an overall score for an entity;
using the plurality of different types of computational models to generate a plurality of scores for the entity; and
determining the overall score for the entity based on the plurality of scores.

9. The method of claim 8 further comprising receiving, from the client device and through the tool, a set of field definitions, wherein generating the plurality of different types of computational models is further based on the set of field definitions.

10. The method of claim 9, wherein a field definition in the set of field definitions specifies a name, a category in the plurality of different categories, and a field type.

11. The method of claim 10, wherein the field definition specifies the field type as a text field type, wherein the field definition further specifies a set of mappings between a set of text values and a set of values.

12. The method of claim 10, wherein the field definition specifies the field type as a numeric field type, wherein the field definition further specifies a weight, a low threshold value, and a high threshold value.

13. The method of claim 8, wherein the plurality of threshold values for the plurality of different categories is a first plurality of threshold values, wherein the method further comprises receiving, from the client device and through the tool, a second plurality of threshold values for the plurality of different categories, wherein generating the plurality of different types of computational models is further based on the second plurality of threshold values for the plurality of different categories.

14. The method of claim 8 further comprising receiving, from the client device and through the tool, a first threshold value for an overall score and a second threshold value for the overall score, wherein generating the plurality of different types of computational models is further based on the first threshold value for the overall score and the second threshold value for the overall score.

15. A system comprising:
a set of processing units; and
a non-transitory machine-readable medium storing instructions that when executed by at least one processing unit in the set of processing units cause the at least one processing unit to:
provide a client device a tool for configuring computational models;
receive, from the client device and through the tool, a selection of a set of different external data sources;
receive, from the client device and through the tool, a plurality of weight values for a plurality of different categories;
receive, from the client device and through the tool, a plurality of threshold values for the plurality of different categories;
generate a plurality of different types of computational models based on the set of different external data sources, the plurality of weight values for the plurality of different categories, and the plurality of threshold values for the plurality of different categories, wherein each computational model in the plurality of different types of computational models is configured to generate a score associated with a category in the plurality of different categories;
receive, from the client device, a request for an overall score for an entity;

use the plurality of different types of computational models to generate a plurality of scores for the entity; and determine the overall score for the entity based on the plurality of scores.

16. The system of claim 15, wherein the instructions further cause the at least one processing unit to receive, from the client device and through the tool, a set of field definitions, wherein generating the plurality of different types of computational models is further based on the set of field definitions.

17. The system of claim 16, wherein a field definition in the set of field definitions specifies a name, a category in the plurality of different categories, and a field type.

18. The system of claim 17, wherein the field definition specifies the field type as a text field type, wherein the field definition further specifies a set of mappings between a set of text values and a set of values.

19. The system of claim 17, wherein the field definition specifies the field type as a numeric field type, wherein the field definition further specifies a weight, a low threshold value, and a high threshold value.

20. The system of claim 15, wherein the plurality of threshold values for the plurality of different categories is a first plurality of threshold values, wherein the instructions further cause the at least one processing units to receive, from the client device and through the tool, a second plurality of threshold values for the plurality of different categories, wherein generating the plurality of different types of computational models is further based on the second plurality of threshold values for the plurality of different categories.

* * * * *